(12) United States Patent
Desrosiers et al.

(10) Patent No.: US 11,311,399 B2
(45) Date of Patent: Apr. 26, 2022

(54) LOCK AND RELEASE MECHANISMS FOR TRANS-CATHETER IMPLANTABLE DEVICES

(71) Applicant: Edwards Lifesciences Corporation, Irvine, CA (US)

(72) Inventors: John J. Desrosiers, San Clemente, CA (US); Daniel James Murray, Orange, CA (US); Michael G. Valdez, Riverside, CA (US); Liron Tayeb, Peduel (IL); David Maimon, Atlit (IL); Eitan Atias, Tel Aviv (IL); Adi Carmi, Ganei Tikva (IL)

(73) Assignee: Edwards Lifesciences Corporation, Irvine, CA (US)

( * ) Notice: Subject to any disclaimer, the term of this patent is extended or adjusted under 35 U.S.C. 154(b) by 101 days.

(21) Appl. No.: 16/716,027

(22) Filed: Dec. 16, 2019

(65) Prior Publication Data

US 2020/0113719 A1   Apr. 16, 2020

Related U.S. Application Data

(63) Continuation of application No. PCT/US2018/040337, filed on Jun. 29, 2018.
(Continued)

(51) Int. Cl.
*A61F 2/966* (2013.01)
*A61B 17/34* (2006.01)
(Continued)

(52) U.S. Cl.
CPC .......... *A61F 2/966* (2013.01); *A61B 17/3468* (2013.01); *A61F 2/2436* (2013.01);
(Continued)

(58) Field of Classification Search
CPC ................... A61F 2/966; A61F 2/2436; A61F 2002/9665; A61F 2230/001;
(Continued)

(56) References Cited

U.S. PATENT DOCUMENTS 519,297 A    5/1894 Bauer
4,035,849 A  7/1977 Angell et al.
(Continued)

FOREIGN PATENT DOCUMENTS

DE    19532846 A1    3/1997
DE    19907646 A1    8/2000
(Continued)

*Primary Examiner* — Richard G Louis
(74) *Attorney, Agent, or Firm* — Edwards Lifesciences

(57) ABSTRACT

Delivery systems and catheters including lock and release connectors for implantable devices and methods for retaining, positioning, and deploying a medical device are disclosed. The lock and release connectors can include a body and at least one door engaged with the body, wherein the door is moveable from a first position to a second position. The lock and release connectors can further include at least one fastener connecting at least one end of the door to the body. The door can be integral with the body or connected and can comprise a shape memory material and/or other materials.

36 Claims, 35 Drawing Sheets

Related U.S. Application Data

(60) Provisional application No. 62/527,577, filed on Jun. 30, 2017.

(51) Int. Cl.
*A61F 2/24* (2006.01)
*A61B 17/12* (2006.01)
*A61N 1/39* (2006.01)

(52) U.S. Cl.
CPC ............... *A61B 2017/12054* (2013.01); *A61F 2002/9665* (2013.01); *A61F 2230/001* (2013.01); *A61M 2205/0266* (2013.01); *A61N 1/3956* (2013.01)

(58) Field of Classification Search
CPC ...... A61F 2220/0075; A61F 2002/9534; A61F 2002/9528; A61F 2/915; A61F 2/07; A61F 2/2418; A61F 2250/0039; A61B 17/3468; A61B 2017/12054; A61M 2205/0266; A61N 1/3956
See application file for complete search history.

(56) References Cited

U.S. PATENT DOCUMENTS

| | | |
|---|---|---|
| 4,592,340 A | 6/1986 | Boyles |
| 4,790,843 A | 12/1988 | Carpentier et al. |
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |
| 5,266,073 A | 11/1993 | Wall |
| 5,325,845 A | 7/1994 | Adair |
| 5,358,496 A | 10/1994 | Ortiz et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,273,909 B1 | 8/2001 | Kugler et al. |
| 6,379,372 B1 | 4/2002 | Dehdashtian et al. |
| 6,383,171 B1 | 5/2002 | Gifford et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,579,305 B1 | 6/2003 | Lashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,764,504 B2 | 7/2004 | Wang et al. |
| 6,767,362 B2 | 7/2004 | Schreck |
| 6,776,791 B1 * | 8/2004 | Stallings .................. A61F 2/95 623/1.11 |
| 6,797,002 B2 | 9/2004 | Spence et al. |
| 6,830,584 B1 | 12/2004 | Seguin |
| 6,887,268 B2 | 5/2005 | Butaric et al. |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,445,632 B2 | 11/2008 | McGuckin, Jr. et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,637,946 B2 | 12/2009 | Solem et al. |
| 7,708,775 B2 | 5/2010 | Rowe et al. |
| 7,737,060 B2 | 6/2010 | Strickler et al. |
| 7,780,723 B2 | 8/2010 | Taylor |
| 7,785,366 B2 | 8/2010 | Maurer et al. |
| 7,951,195 B2 | 5/2011 | Antonsson et al. |
| 7,959,661 B2 | 6/2011 | Hijlkema et al. |
| 8,029,556 B2 | 10/2011 | Rowe |
| 8,142,492 B2 | 3/2012 | Forster et al. |
| 8,167,932 B2 | 5/2012 | Bourang et al. |
| 8,236,049 B2 | 8/2012 | Rowe et al. |
| RE43,882 E | 12/2012 | Hopkins et al. |
| 8,323,335 B2 | 12/2012 | Rowe et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,475,523 B2 | 7/2013 | Duffy |
| 8,568,472 B2 | 10/2013 | Marchand et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,685,086 B2 | 4/2014 | Navia et al. |
| 8,734,507 B2 | 5/2014 | Keranen |
| 8,801,776 B2 | 8/2014 | House et al. |
| 9,061,119 B2 | 6/2015 | Le et al. |
| 9,078,747 B2 | 7/2015 | Conklin |
| 9,095,434 B2 | 8/2015 | Rowe |
| 9,119,716 B2 | 9/2015 | Lee et al. |
| 9,119,718 B2 | 9/2015 | Keranen |
| 9,192,471 B2 | 11/2015 | Bolling |
| 9,237,886 B2 | 1/2016 | Seguin et al. |
| 9,314,335 B2 | 4/2016 | Konno |
| 9,364,326 B2 | 6/2016 | Yaron |
| 9,463,268 B2 | 10/2016 | Spence |
| 9,474,599 B2 | 10/2016 | Keranen |
| 9,597,205 B2 | 3/2017 | Tuval |
| 9,622,863 B2 | 4/2017 | Karapetian et al. |
| 9,795,477 B2 | 10/2017 | Tran et al. |
| 10,786,351 B2 | 9/2020 | Christianson et al. |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |

(56) References Cited

U.S. PATENT DOCUMENTS

| | | |
|---|---|---|
| 2002/0107535 A1 | 8/2002 | Wei et al. |
| 2002/0107536 A1 | 8/2002 | Hussein |
| 2002/0151970 A1 | 10/2002 | Garrison et al. |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0093087 A1 | 5/2003 | Jones et al. |
| 2003/0120341 A1 | 6/2003 | Shennib et al. |
| 2003/0130611 A1 | 7/2003 | Martin |
| 2003/0225420 A1 | 12/2003 | Wardle |
| 2004/0093061 A1 | 5/2004 | Acosta et al. |
| 2004/0111006 A1 | 6/2004 | Alferness et al. |
| 2004/0133263 A1 | 7/2004 | Dusbabek et al. |
| 2004/0143197 A1 | 7/2004 | Soukup et al. |
| 2004/0148008 A1* | 7/2004 | Goodson, IV .......... A61F 2/966 623/1.12 |
| 2004/0186563 A1 | 9/2004 | Lobbi |
| 2004/0186565 A1 | 9/2004 | Schreck |
| 2004/0204749 A1* | 10/2004 | Gunderson .............. A61F 2/91 623/1.12 |
| 2004/0260389 A1 | 12/2004 | Case et al. |
| 2005/0043790 A1 | 2/2005 | Seguin |
| 2005/0080474 A1 | 4/2005 | Andreas et al. |
| 2005/0096736 A1 | 5/2005 | Osse et al. |
| 2005/0119682 A1 | 6/2005 | Nguyen et al. |
| 2005/0119735 A1 | 6/2005 | Spence et al. |
| 2005/0137689 A1 | 6/2005 | Salahieh et al. |
| 2005/0137691 A1 | 6/2005 | Salahieh et al. |
| 2005/0149160 A1 | 7/2005 | McFerran |
| 2005/0182483 A1 | 8/2005 | Osborne et al. |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2005/0283231 A1 | 12/2005 | Haug et al. |
| 2006/0025857 A1 | 2/2006 | Bergheim et al. |
| 2006/0173524 A1 | 8/2006 | Salahieh et al. |
| 2006/0195134 A1 | 8/2006 | Crittenden |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0112422 A1 | 5/2007 | Dehdashtian |
| 2007/0142906 A1 | 6/2007 | Figulla et al. |
| 2007/0186933 A1 | 8/2007 | Domingo et al. |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2007/0293808 A1 | 12/2007 | Williams et al. |
| 2008/0004696 A1 | 1/2008 | Vesely |
| 2008/0033542 A1 | 2/2008 | Antonsson et al. |
| 2008/0065011 A1 | 3/2008 | Marchand et al. |
| 2008/0077235 A1 | 3/2008 | Kirson |
| 2008/0125853 A1 | 5/2008 | Bailey et al. |
| 2008/0188923 A1 | 8/2008 | Chu |
| 2008/0208330 A1 | 8/2008 | Keranen |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0192601 A1 | 7/2009 | Rafiee et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0036484 A1 | 2/2010 | Hariton et al. |
| 2010/0049313 A1 | 2/2010 | Alon et al. |
| 2010/0063573 A1 | 3/2010 | Hijlkema et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0145440 A1 | 6/2010 | Keranen |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0249894 A1 | 9/2010 | Oba et al. |
| 2010/0249923 A1 | 9/2010 | Alkhatib et al. |
| 2010/0274344 A1 | 10/2010 | Dusbabek et al. |
| 2010/0298927 A1 | 11/2010 | Greenberg |
| 2010/0312333 A1 | 12/2010 | Navia et al. |
| 2010/0318184 A1 | 12/2010 | Spence |
| 2011/0015729 A1 | 1/2011 | Jimenez et al. |
| 2011/0022149 A1 | 1/2011 | Cox et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0041550 A1 | 2/2012 | Salahieh et al. |
| 2012/0059458 A1 | 3/2012 | Buchbinder et al. |
| 2012/0123529 A1 | 5/2012 | Levi et al. |
| 2012/0150287 A1 | 6/2012 | Forster et al. |
| 2012/0239142 A1 | 9/2012 | Liu et al. |
| 2012/0283820 A1 | 11/2012 | Tseng et al. |
| 2013/0030519 A1 | 1/2013 | Tran et al. |
| 2013/0035636 A1 | 2/2013 | Beasley et al. |
| 2013/0190865 A1 | 7/2013 | Anderson |
| 2013/0274855 A1 | 10/2013 | Stante et al. |
| 2013/0310918 A1 | 11/2013 | Taylor et al. |
| 2013/0317598 A1 | 11/2013 | Rowe et al. |
| 2014/0012373 A1 | 1/2014 | Chau et al. |
| 2014/0074299 A1 | 3/2014 | Endou et al. |
| 2014/0081394 A1 | 3/2014 | Keranen et al. |
| 2014/0155996 A1 | 6/2014 | Wilson et al. |
| 2014/0172070 A1 | 6/2014 | Seguin |
| 2014/0222142 A1 | 8/2014 | Kovalsky et al. |
| 2014/0257452 A1 | 9/2014 | Slazas et al. |
| 2014/0296962 A1 | 10/2014 | Cartledge et al. |
| 2014/0316513 A1 | 10/2014 | Tang |
| 2014/0358222 A1 | 12/2014 | Gorman, III et al. |
| 2014/0379074 A1 | 12/2014 | Spence et al. |
| 2015/0025623 A1 | 1/2015 | Granada et al. |
| 2015/0100114 A1 | 4/2015 | Shahriari |
| 2015/0164640 A1 | 6/2015 | McLean et al. |
| 2015/0173897 A1 | 6/2015 | Raanani et al. |
| 2015/0230921 A1 | 8/2015 | Chau et al. |
| 2015/0245910 A1 | 9/2015 | Righini et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |
| 2015/0351904 A1 | 12/2015 | Cooper et al. |
| 2015/0374493 A1 | 12/2015 | Yaron et al. |
| 2016/0015514 A1 | 1/2016 | Lashinski et al. |
| 2016/0074165 A1 | 3/2016 | Spence et al. |
| 2016/0095705 A1 | 4/2016 | Keranen et al. |
| 2016/0143732 A1 | 5/2016 | Glimsdale |
| 2016/0184095 A1 | 6/2016 | Spence et al. |
| 2016/0199177 A1 | 7/2016 | Spence et al. |
| 2016/0256276 A1 | 9/2016 | Yaron |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0065415 A1 | 3/2017 | Rupp et al. |
| 2017/0217385 A1 | 8/2017 | Rinkleff et al. |
| 2017/0231756 A1 | 8/2017 | Armer et al. |
| 2017/0266005 A1 | 9/2017 | McGuckin, Jr. |
| 2017/0273788 A1 | 9/2017 | O'Carroll et al. |
| 2017/0273789 A1 | 9/2017 | Yaron et al. |
| 2017/0281337 A1 | 10/2017 | Campbell |
| 2018/0000580 A1 | 1/2018 | Wallace |
| 2018/0085217 A1 | 3/2018 | Lashinski et al. |
| 2018/0153689 A1 | 6/2018 | Maimon et al. |
| 2018/0206074 A1 | 7/2018 | Tanasa et al. |
| 2018/0289481 A1 | 10/2018 | Dolan |
| 2018/0303606 A1 | 10/2018 | Rothstein et al. |

(56) References Cited

U.S. PATENT DOCUMENTS

| | | |
|---|---|---|
| 2018/0318073 A1 | 11/2018 | Tseng et al. |
| 2018/0318080 A1 | 11/2018 | Quill et al. |
| 2018/0344456 A1 | 12/2018 | Barash et al. |
| 2020/0205962 A1 | 7/2020 | Karavany et al. |

FOREIGN PATENT DOCUMENTS

| | | |
|---|---|---|
| EP | 0592410 B1 | 10/1995 |
| EP | 0850607 A1 | 7/1998 |
| EP | 1432369 A1 | 6/2004 |
| EP | 1521550 A2 | 4/2005 |
| EP | 1296618 B1 | 1/2008 |
| EP | 1827314 B1 | 12/2010 |
| EP | 2620125 A1 | 7/2013 |
| EP | 2726018 A2 | 5/2014 |
| EP | 2806829 A2 | 12/2014 |
| FR | 2815844 A1 | 5/2002 |
| WO | 9117720 A1 | 11/1991 |
| WO | 9829057 A1 | 7/1998 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 53028558 A2 | 4/2003 |
| WO | 03047468 A1 | 6/2003 |
| WO | 2004019825 A1 | 3/2004 |
| WO | 2005084595 A1 | 9/2005 |
| WO | 2006011127 A2 | 2/2006 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2009155561 A2 | 12/2009 |
| WO | 2010121076 A2 | 10/2010 |
| WO | 2012009006 A1 | 1/2012 |
| WO | 2012063228 A1 | 5/2012 |
| WO | 2013059747 A1 | 4/2013 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016128983 A1 | 8/2016 |
| WO | 2016130820 A1 | 8/2016 |
| WO | 2017103833 A1 | 6/2017 |

\* cited by examiner

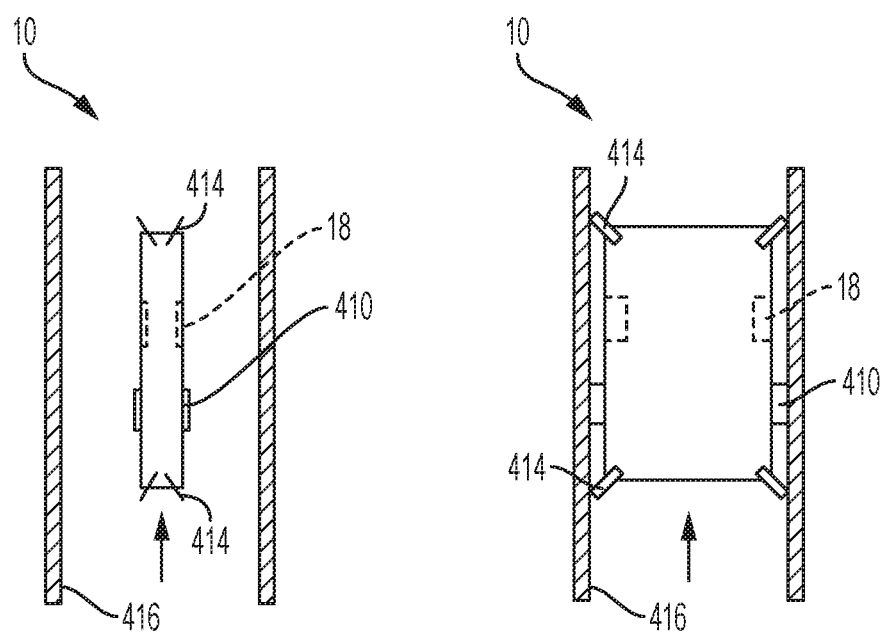

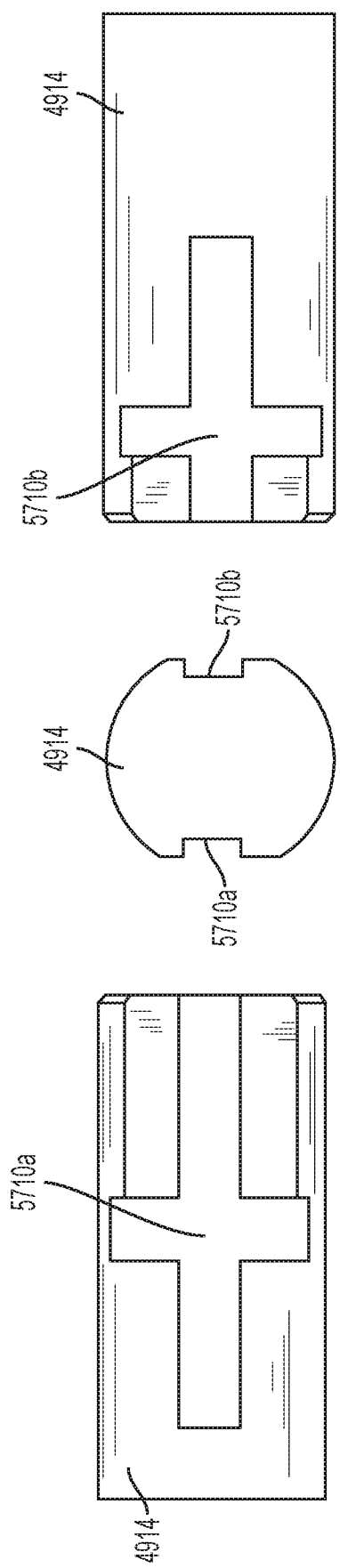

LOCK AND RELEASE MECHANISMS FOR TRANS-CATHETER IMPLANTABLE DEVICES

CROSS-REFERENCE TO RELATED APPLICATIONS

The present application is a continuation of International Application No. PCT/US2018/040337 filed on Jun. 29, 2018, which claims priority to U.S. Provisional Patent Application No. 62/527,577, filed Jun. 30, 2017, and is related to U.S. patent application Ser. No. 15/422,354, filed Feb. 1, 2017, which claims priority to U.S. Provisional Patent Application No. 62/292,142, filed Feb. 5, 2016, the entire disclosures of the foregoing are incorporated herein by reference as though recited herein in their entirety.

FIELD OF THE INVENTION

The present invention relates to delivery systems for implantable devices and, including lock and release mechanisms for implantable medical devices that can be used with a trans-catheter delivery system for use in canals, vessels, lumens, passageways, or cavities of the anatomy including the heart and vasculature. Trans-catheter implantable devices include docking stations, cardiac valve implants such as replacement valves and trans-catheter heart valves ("THV"), stents, annuloplasty rings, other annuloplasty implants, etc.

BACKGROUND OF THE INVENTION

Implantable medical devices can be used in many different parts of the body for various applications, including orthopedics, pacemakers, cardiovascular stents, defibrillators or neural prosthetics. A trans-catheter technique can be used for introducing and implanting a prosthetic heart valve or other medical devices using a flexible catheter in a manner that is less invasive than open heart or other traditional surgeries. In this technique, a medical device can be mounted in a crimped state on the end portion of a flexible catheter and advanced through a blood vessel, canal, or other body passageways until the device reaches the implantation site. The device at the catheter tip can then be expanded to its functional size at the intended implantation site, such as by inflating a balloon on which the device is mounted. Optionally, the device can have a resilient, self-expanding stent or frame that expands the device to its functional size when it is advanced from a delivery sheath at the distal end of the catheter. The implantable medical devices are maintained in the catheter until there are deployed and expanded in the patient.

SUMMARY

This summary is meant to provide examples and is not intended to be limiting of the scope of the invention in any way. For example, any feature included in an example of this summary is not required by the claims, unless the claims explicitly recite the feature. The description discloses exemplary embodiments of lock and release connectors for trans-catheter implantable devices and catheters for medical device implantation. The lock and release connectors and catheters can be constructed in a variety of ways.

In one exemplary embodiment, a lock and release connector for a trans-catheter implantable device can comprise a body and at least one door engaged with the body, wherein the door is moveable from a first position to a second position. Optionally, the door can be integral with the body. In some exemplary embodiments, the door can be connected to the body. Optionally, the door can be hingedly connected to the body. The door can be constructed in a variety of ways and can comprise a variety of different materials, e.g., the door can comprises a nickel titanium alloy. The lock and release connector can further comprise one fastener or multiple fasteners connecting at least one portion or end of the door to the body.

In one exemplary embodiment, a system and/or catheter comprises an outer tube having a distal opening. An inner tube can be disposed in the outer tube. An implantable medical device is disposed in the outer tube wherein the medical device has an extension. A lock and release connector having a body and a door is engaged with the body. The door is moveable from a first position to a second position. If an inner tube is used, the lock and release connector can be connected to the inner tube. The extension can be interposed between the body and the door. Optionally, the implantable medical device can further comprise at least a second extension. In some exemplary embodiments, the lock and release connector further comprises a second door. Optionally, the implantable medical device can be a docking station. The body can be hingedly connected to the door.

In one exemplary embodiment, a method for positioning a medical device comprises connecting a lock and release connector to an inner tube of a catheter. The method can further include placing the inner tube inside an outer tube of the catheter. Additionally, an extension can be interposed at a proximal end of the medical device between a body and a door of a lock and release connector that is connected to the inner tube. The method can further include positioning the medical device in the outer tube of the catheter and positioning a distal end of the catheter at a delivery site. Additionally, the outer tube can be displaced with respect to or relative to the inner tube and the lock and release connector until a distal end of the medical device is positioned outside the outer tube. The method can further include continuing to displace the outer tube with respect to or relative to the inner tube and the lock and release connector until the door opens and releases the extension from between the body and the door. Additionally, the proximal end of the medical device and the extension can be deployed to the delivery site. In some exemplary embodiments, the method further comprises returning the lock and release connector to a position inside the outer tube.

Various features as described elsewhere in this disclosure can be included in the examples summarized here and various methods and steps for using the examples and features can be used, including as described elsewhere herein and in various combinations.

Further understanding of the nature and advantages of the disclosed inventions can be obtained from the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. These drawings depict only typical embodiments of the present disclosure and are therefore not to be considered limiting of the scope of the disclosure. Moreover, while the figures might be drawn to scale for some embodiments, the figures are not necessarily drawn to scale for all embodiments. Embodiments of the present disclosure will be described and explained with additional specificity and detail through the use of the accompanying drawings.

FIG. 2A is a schematic illustration of a compressed medical device being positioned in a circulatory system;

FIG. 2B is a schematic illustration of the medical device of FIG. 2A expanded to set the position of the medical device in the circulatory system;

FIG. 30A is a left side view of an exemplary embodiment of a connector body useable with the frame of FIG. 9A;

FIG. 30B is a front view of the connector of FIG. 30A;

FIG. 30C is a right side view of the connector of FIG. 30A;

FIG. 30D is a perspective view of an exemplary embodiment of a first door of the connector of FIGS. 30A through 30C; and FIG. 30E is a perspective view of an exemplary embodiment of a door of the connector of FIGS. 30A through 30C.

DETAILED DESCRIPTION

Figure 1A:
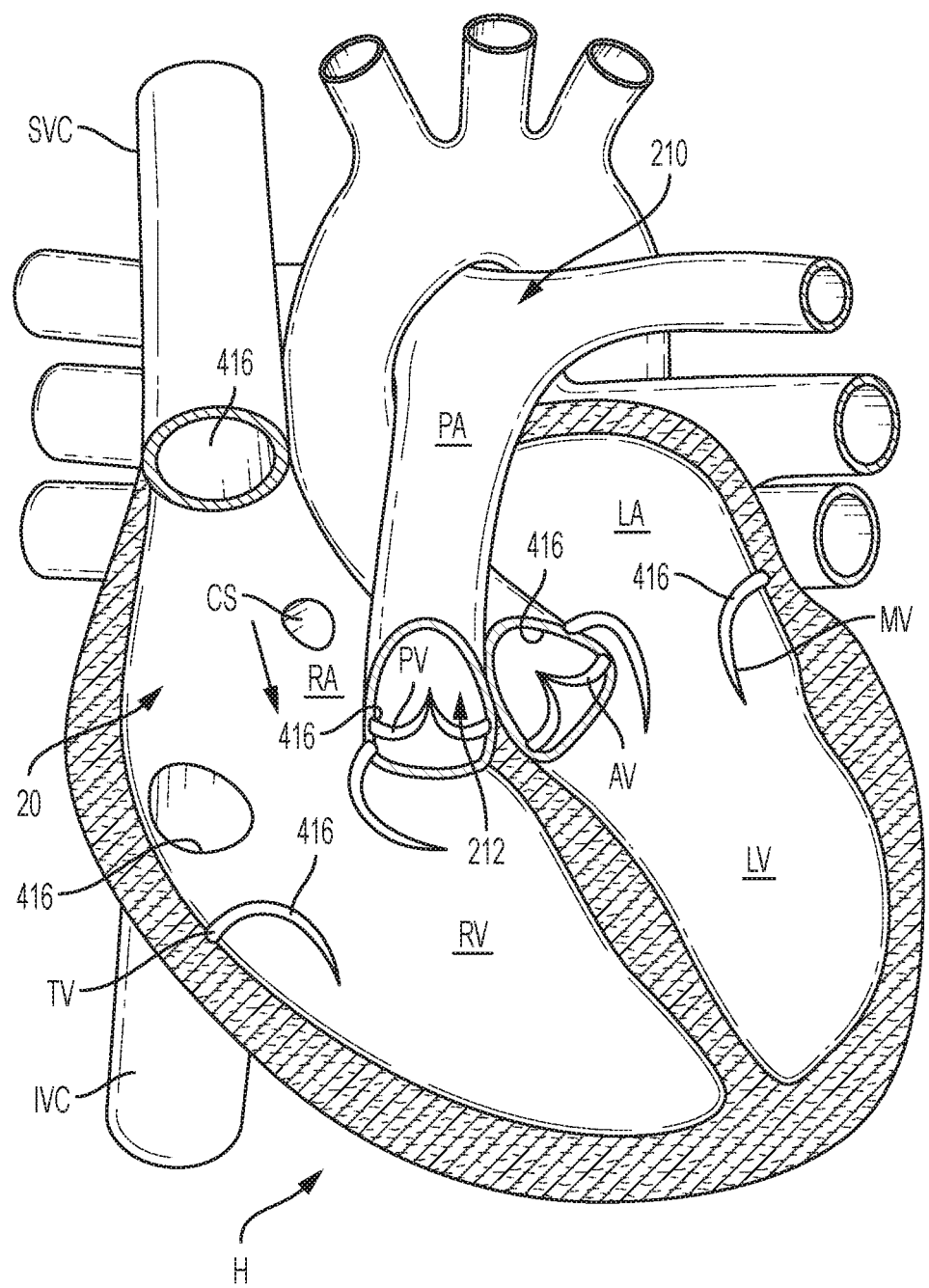
FIG. 1A is a cutaway view of the human heart in a diastolic phase.
Figure 1B:
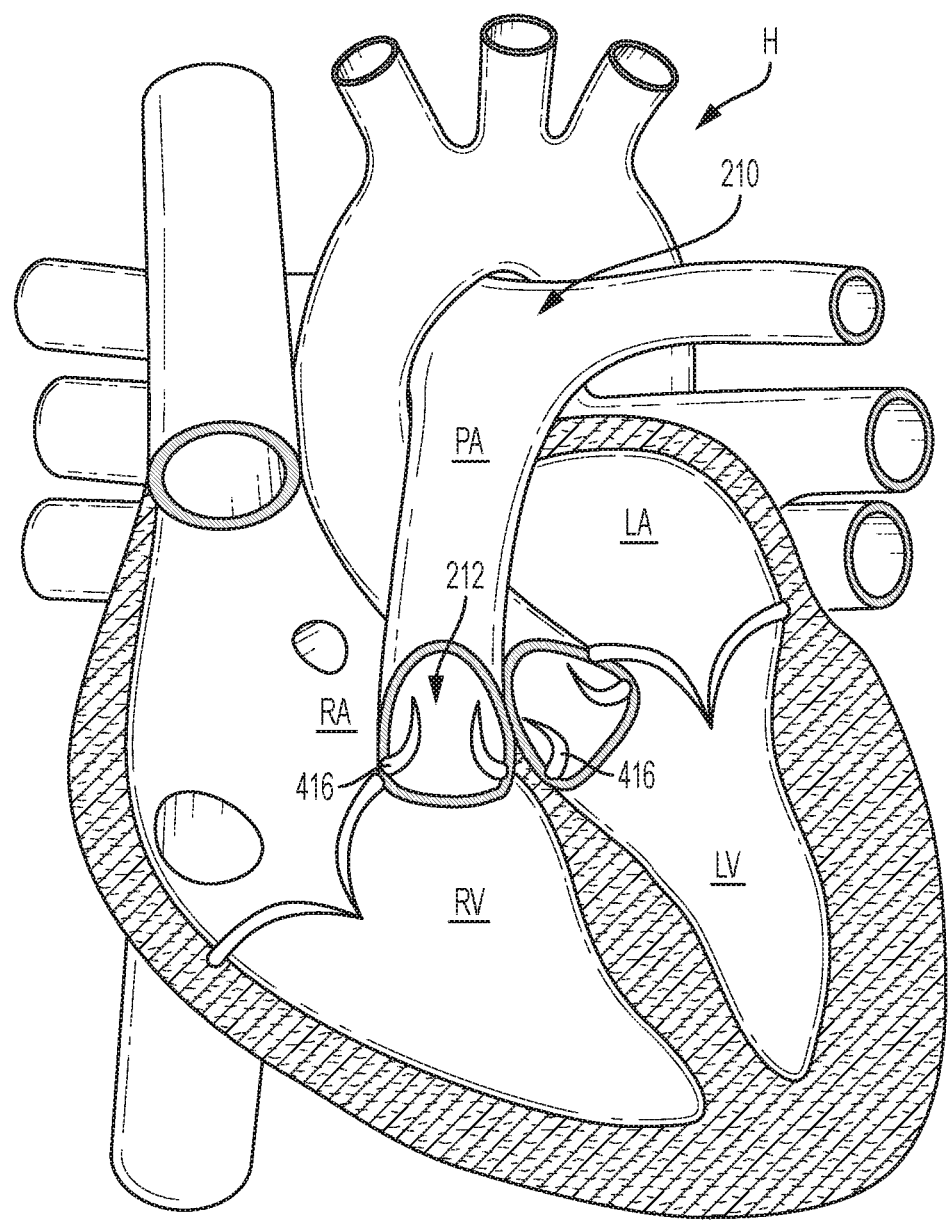
FIG. 1B is a cutaway view of the human heart in a systolic phase.

The following description refers to the accompanying drawings, which illustrate specific embodiments of the invention. Other embodiments having different structures and operation do not depart from the scope of the present invention. Exemplary embodiments of the present disclosure are directed to lock and release connectors (see e.g., lock and release connectors 7000 in FIGS. 15A and 15B) for implantable medical devices 10 (e.g., for trans-catheter implantable devices) and catheters, systems, and assemblies for medical device implantation. In some exemplary embodiments, the medical devices 10 are illustrated as being docking stations, e.g., docking stations for THVs used within the pulmonary artery. However, the lock and release connectors described and shown herein can be used for various medical devices in other areas of the anatomy, including for orthopedics, pacemakers, cardiovascular stents, grafts, coils, defibrillators, neural prosthetics and for use in many other canals, lumens, vessels, passageways, or cavities of the anatomy, including those in the heart and vasculature. The use of the lock and release connectors and the inventive concepts disclosed herein is only limited by the creativity of the designer.

FIGS. 1A-12D show a human heart and illustrate examples of medical devices with which the lock and release mechanism 7000 can be used, and these figures are discussed in more detail later in this disclosure. The implantable medical devices illustrated in FIGS. 2A-12D are only examples of the many types of medical devices with which the lock and release connectors 7000 can be utilized. FIGS. 1A-12D are taken from pending U.S. application Ser. No. 15/422,354, which is incorporated herein by reference in its entirety. FIGS. 1A-14C are described in more detail below to provide examples of applications for the lock and release mechanisms and associated concepts.

It should be noted that various embodiments of lock and release connectors (see e.g., lock and release connectors 7000 in FIGS. 15A and 15B), medical devices, and anchors/extensions on medical devices are disclosed herein, and any combination of the various features and options described or shown herein can be made unless specifically excluded. For example, any of the lock and release connectors disclosed, can be used with any type of medical device, valve, and/or any delivery system, even if a specific combination is not explicitly described. Likewise, the different constructions of lock and release connectors and medical devices can be mixed and matched, such as by combining any lock and release connector type/feature, medical device type/feature, etc., even if not explicitly disclosed. In short, individual components of the disclosed systems can be combined unless mutually exclusive or otherwise physically impossible.

For the sake of uniformity, in these Figures and others in the application the medical devices, such as docking stations are depicted such that the pulmonary bifurcation end is up, while the ventricular end is down. These directions can also be referred to as "distal" as a synonym for far, up, and/or the pulmonary bifurcation end, and "proximal" as a synonym for near, down, and/or the ventricular end, which are terms relative to the physician's perspective.

FIGS. 11A, 11B and 12A-12D illustrate a distal portion of an exemplary embodiment of a catheter 3600 for delivering and deploying an implantable medical device 10. In the exemplary embodiment, the medical device 10 is described and discussed herein as being a docking station, but the frame/covered frame is also representative of a stent, stent frame, stent-graft, a frame including a valve (e.g., representative of a transcatheter heart valve THV), and other medical devices. The catheter 3600 can take a wide variety of different forms. In the illustrated example, the catheter 3600 includes an outer tube/sleeve 4910, an inner tube/sleeve 4912, a connector 4914 that is connected to the inner tube 4912, and an elongated nosecone 28 that is connected to the connector 4914 by a connecting tube 4916. In the some embodiments, the connector 4914 is a lock and release connector 7000. (See e.g., FIGS. 15A and 15B). While the implantable medical device 10 is described/discussed as a docking station, any medical device can be used. Inner tube 4912 can be disposed in the outer tube 4910.

The implantable medical device 10 can be disposed in the outer tube 4910. (See FIG. 11B). Extensions 5000 can connect the medical device 10 to the connector 4914, which can be a lock and release connector 7000 described herein or a connector that incorporates the inventive concepts described herein. The extensions 5000 can be retaining portions that are longer than the remainder of the retaining portions 414. (See FIG. 12C-12D). The catheter 3600 can include a guidewire lumen 6390 and be routed over a guidewire 5002 to position the medical device 10 at the delivery site.

Figure 12A:
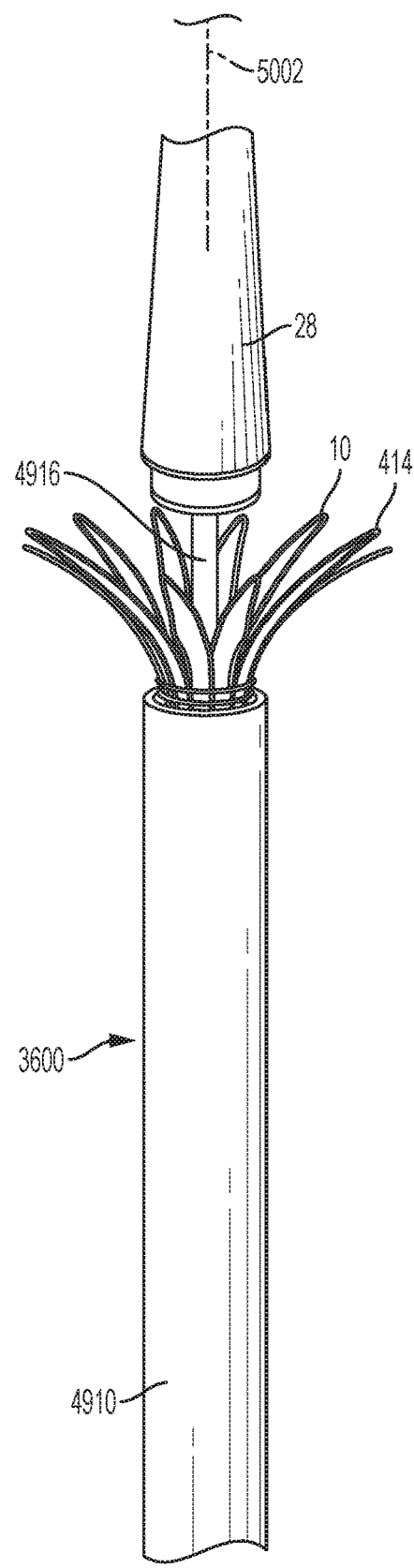
FIGS. 12A-12D illustrate an exemplary deployment of an exemplary implantable medical device from a catheter.
Figure 12B:
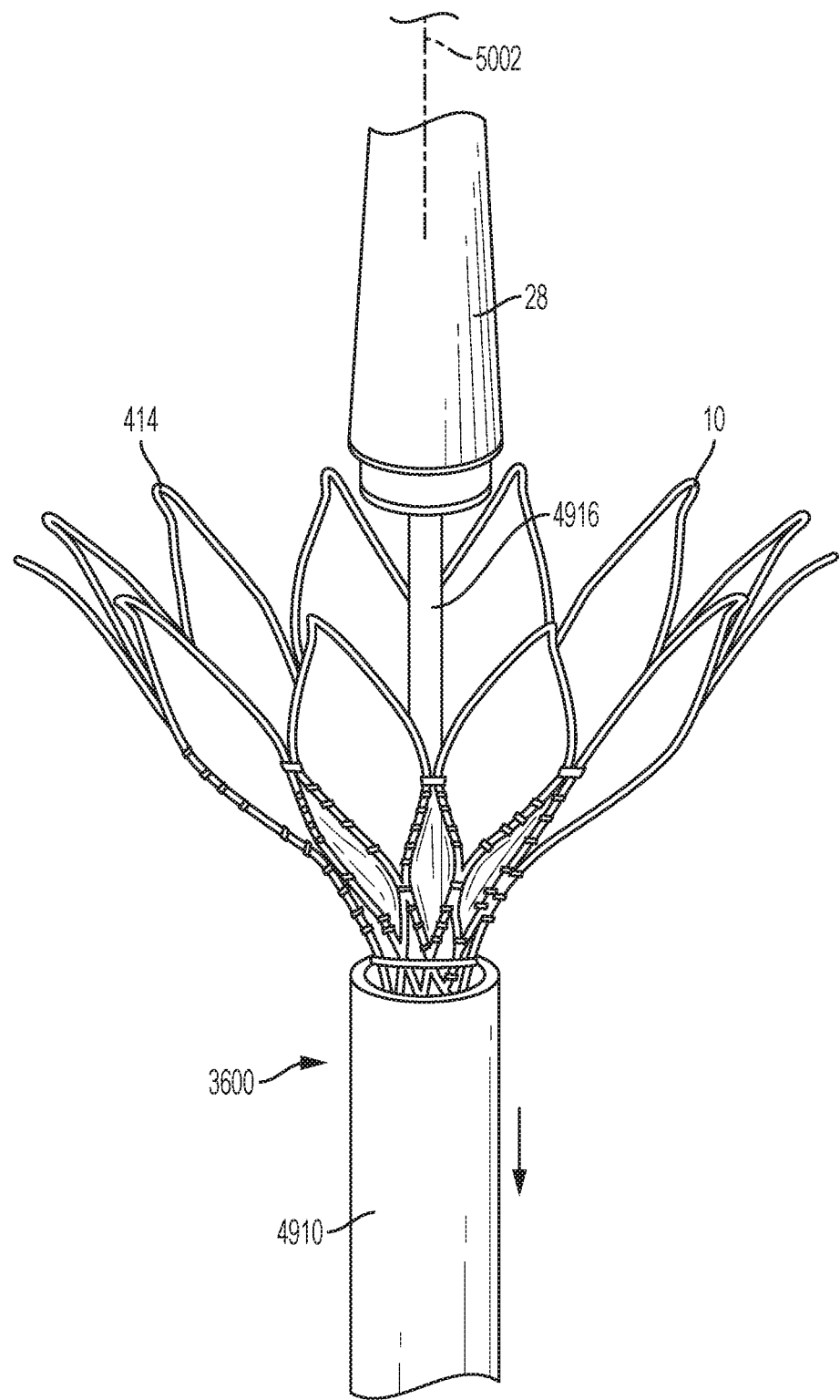
Figure 12C:
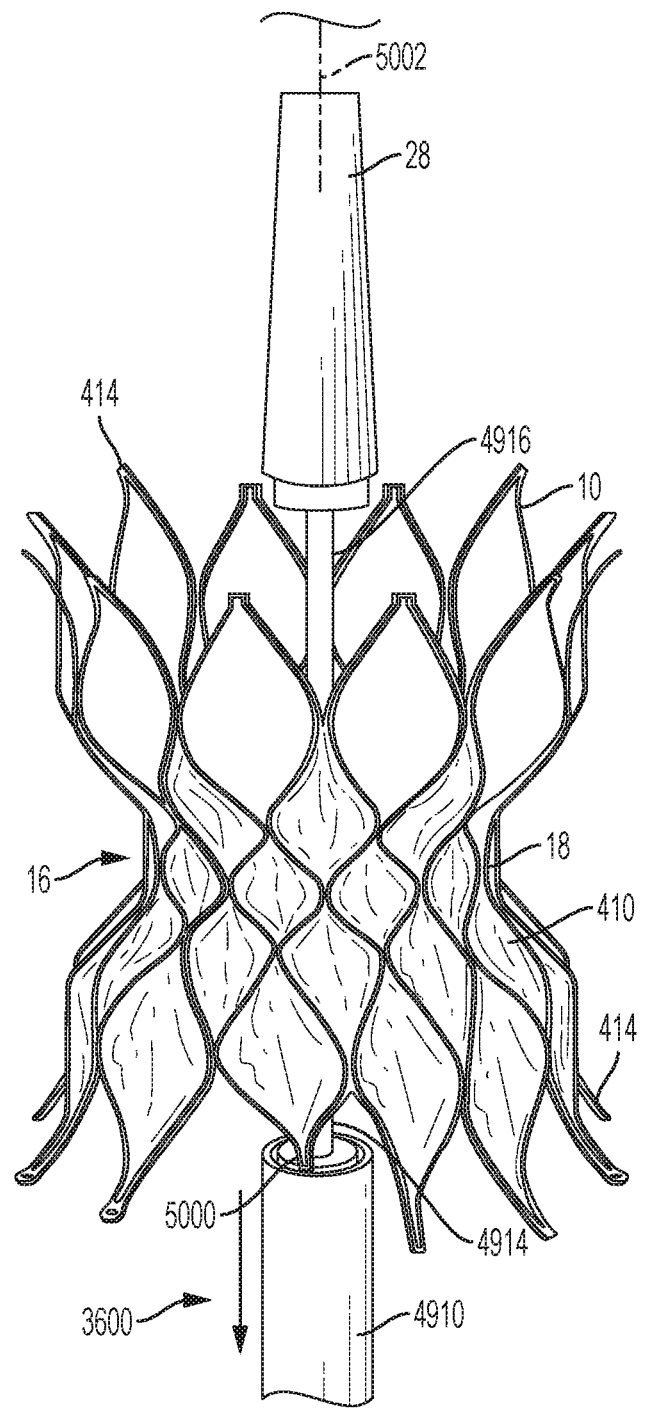
Figure 12D:
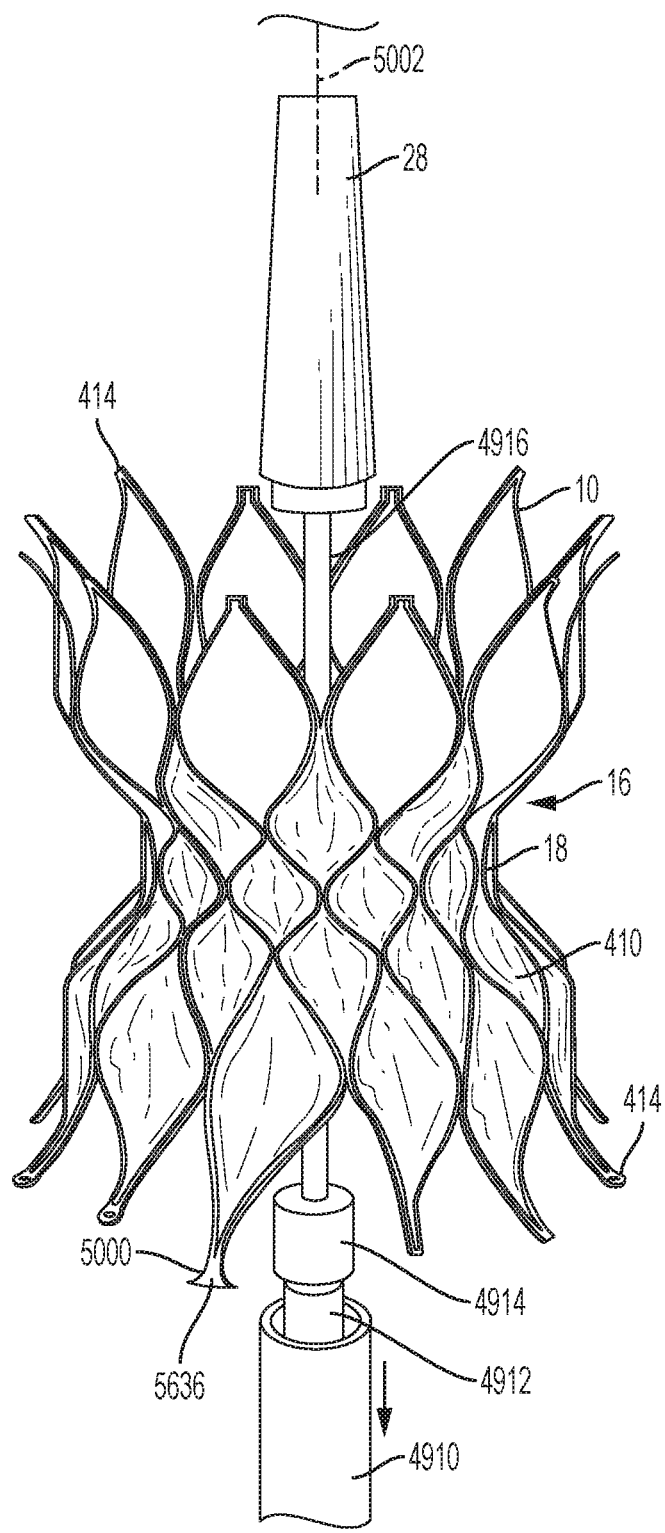

Referring to FIGS. 12A-12D, when the medical device 10 is a docking station or includes an expandable frame, the outer tube 4910 can be progressively retracted with respect to the medical device 10, the inner tube 4912, the connector 4914 (which can be any of the lock and release connectors 7000 described herein or a connector that incorporates the inventive concepts herein), and the elongated nosecone 28 to deploy the medical device 10. While it is preferred to retract the outer tube (as depicted in FIGS. 12A-12D) relative to the medical device, inner tube, nose cone, connector etc. (i.e., while these remain stationary, e.g., stationary relative to a proximal handle), it is also possible to advance the medical device, inner tube, nose cone, and/or connector relative to the outer sheath. In FIG. 12A, the medical device 10 begins to expand from the outer tube 4910. In FIG. 12B, a distal end 14 of the medical device 10 expands from the outer tube 4910. In FIG. 12C, the medical device 10 is expanded out of the outer tube 4910, except the extensions 5000 remain retained by the connector 4914, such as the lock and release connector 7000 in the outer tube 4910. In FIG. 12D, connector 4914, such as a lock and release connector 7000 extends from the outer tube 4910 to release the extensions 5000, thereby allowing the frame to expand and fully deploying the medical device. During deployment of a medical device in the circulatory system, similar steps can be used and the medical device can be deployed in a similar way.

FIGS. 13, 14A, 14B, and 14C illustrate one non-limiting example of how the medical device 10 can be coupled to the connector 4914, specifically the lock and release connector 7000. As is illustrated by FIGS. 12A-12D, when the medical device 10 is pushed out of the outer tube 4910, it self-expands in one exemplary embodiment. One approach to controlling expansion of the medical device 10 is to anchor at least one end, such as the proximal end 12, of the stent to the connector 4914, such as the lock and release connector 7000. This approach allows a distal end 14 of the stent to expand first, without the proximal end expanding (See FIG. 12B). Then when the outer tube/sheath 4910 is moved backward or is retracted relative to the device 10 (or when the stent is moved forward relative to the outer tube 4910), the proximal end 12 disengages from the connector 4914, e.g., the lock and release connector 7000, and the proximal end 12 of the medical device is permitted to expand (See FIG. 12D).

This can be facilitated by including one or more anchors or extensions 5000 on at least the proximal end of the device 10. In the illustrated examples, one or two extensions are included. However, any number of extensions 5000, such as one, two, three, four, five, etc. can be included. The extensions 5000 and/or heads 5636 of the extensions can take a wide variety of different forms, shapes, sizes, etc. The extensions 5000 can engage with the connector 4914, e.g., the lock and release connector 7000, within the outer tube 4910. The extensions 5000 can include a face 5600 and can include heads 5636 with sides 5640 that extend away from a straight portion 5638 at an angle beta β (See FIG. 14B), such as between 30 and 60 degrees. Such heads 5636 can be generally triangular as illustrated or another shape (e.g., round, spherical, rectangular, pyramidal, etc.), for example, the angularly extending sides 5640 can be connected together by another shape, such as a rounded shape, a rectangular shape, pyramidal shape, or another shape. That is, the heads 5636 can function in the same manner as the illustrated triangular head, without being triangular.

Figure 13:
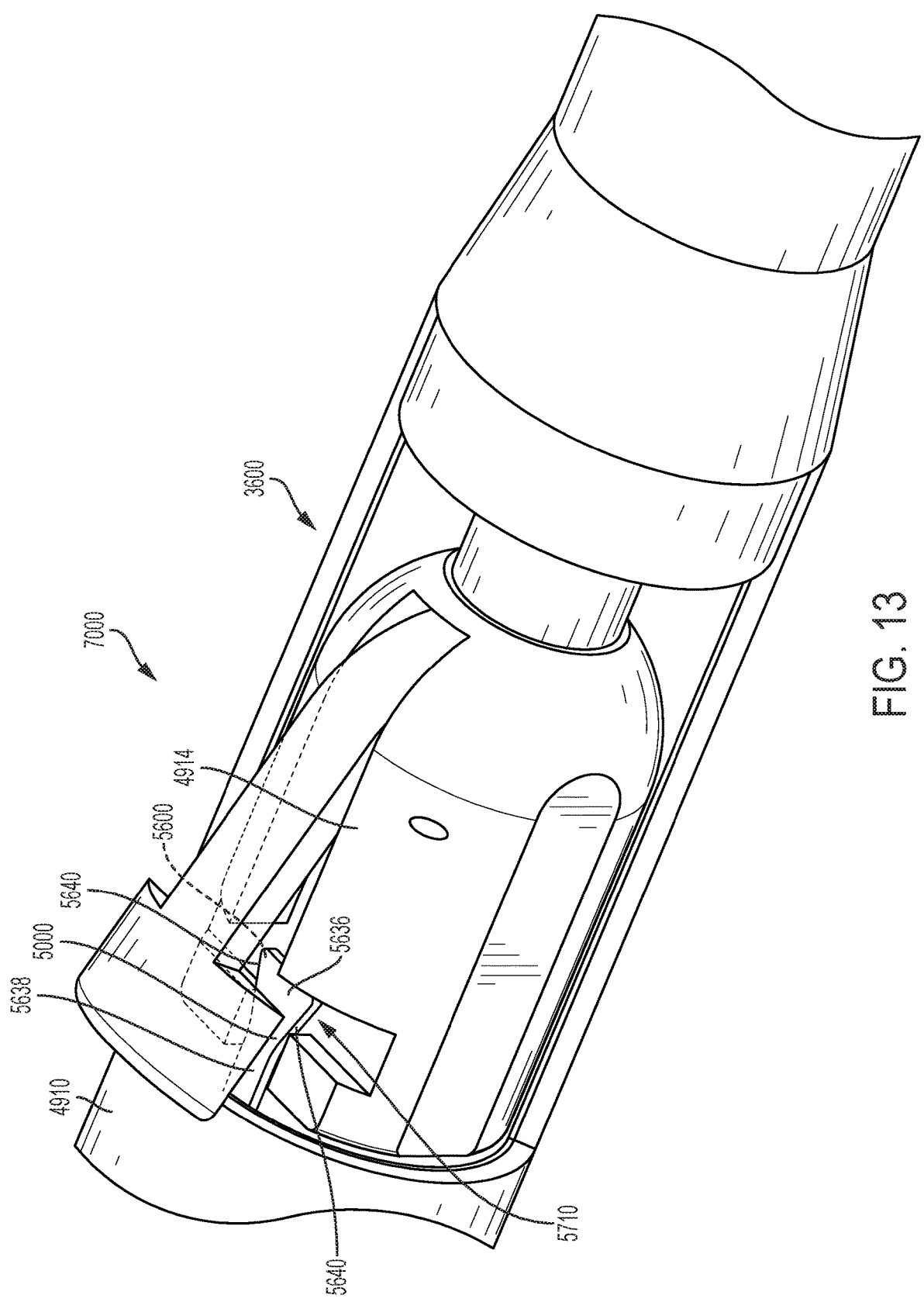
FIG. 13 is a perspective view of a holder for retaining an implantable medical device in a catheter.
Figure 14C:
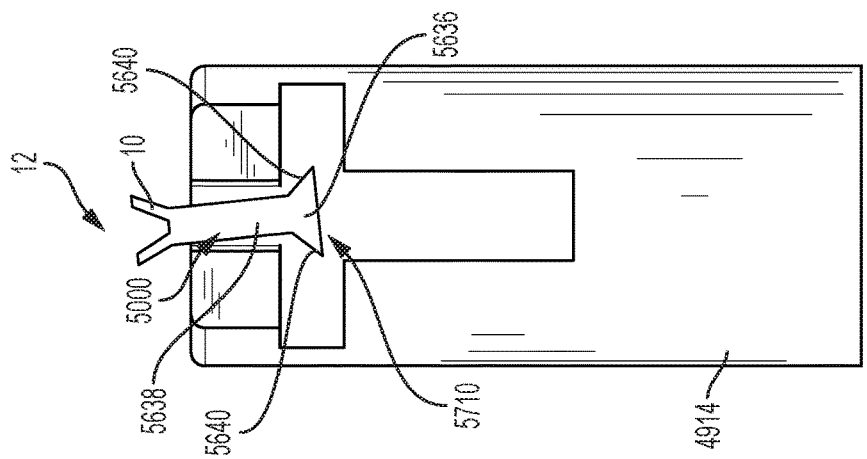
FIGS. 14B and 14C illustrate side views of exemplary extensions of an implantable medical device disposed in the holder.
Figure 14B:
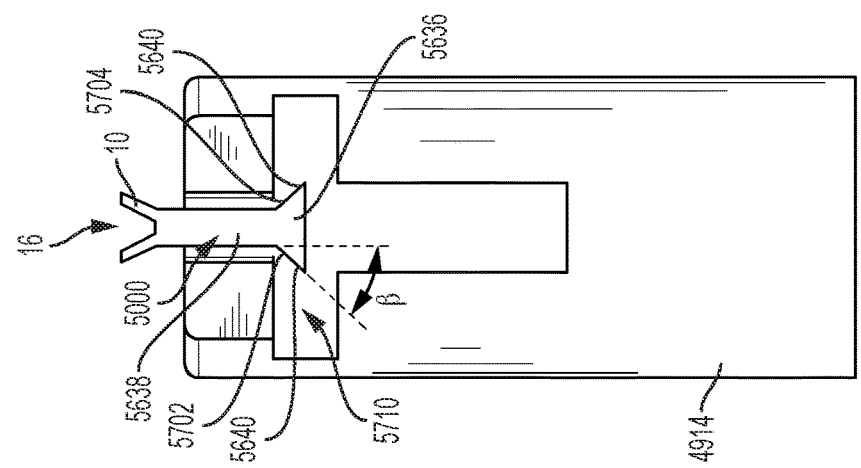
Figure 14A:
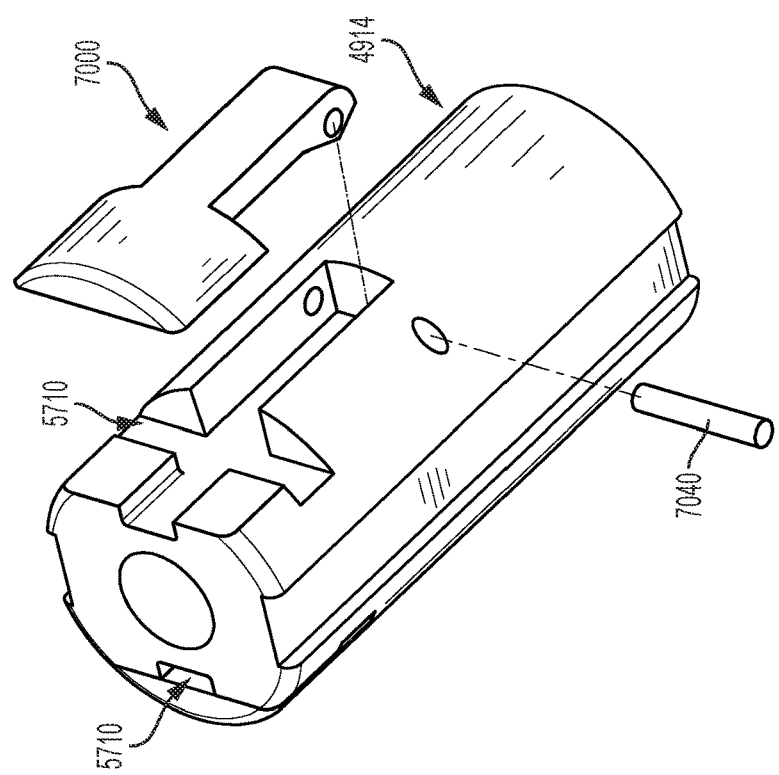
FIG. 14A is a perspective view of a holder for retaining an implantable medical device in a catheter.

Referring to FIGS. 14A and 14B, a head 5636 with sides 5640 that extend away from one another at an angle β, such as a triangular head. Referring to FIGS. 13, 14A, 14B, and 14C, the heads 5636 fit into the T-shaped recesses 5710 in a holder to hold the proximal end 12 of the medical device while the distal end self-expands within the body. The connector 4914, or specifically the lock and release connector 7000, remains in the delivery catheter until moved relatively out of the catheter (e.g., by retracting the outer tube/sleeve 4910 or by advancing the connector 4914, see FIG. 12D). Referring to FIG. 13, the outer tube/sleeve 4910 of the catheter 3600 can be closely disposed over the connector 4914, such that the heads 5636 are captured in the recesses 5710, between the outer tube/sleeve 4910 and the body of the connector 4914 (or between the recesses 5710 and the doors 7020 of the lock and release assembly, see FIG. 22). This capturing in the recesses 5710 holds the end of the medical device 10 as the medical device expands. In this manner, delivery of the medical device 10 is controlled and recapture of at least a partially deployed device is possible (e.g., FIGS. 12A and 12B show examples of partially deployed devices that could be recaptured).

Referring back to FIG. 12D, at the end of the expansion of the medical device 10, when the distal end of the medical device has already expanded, the connector 4914 or lock and release connector 7000 is moved relatively out of the outer sleeve. The heads 5636 are then free to move radially outward and disengage with the respective recesses 5710 (see FIG. 13) or the recesses 5710 and doors 7020 (see FIG. 24B). The heads 5636 can force the doors 7020 open and/or the doors can be opened in other manners as described below. While referred to as "doors" herein, features 7020 can be called latches, locks, arms, hinged portions, or other descriptors.

In one embodiment, all of the extensions 5000 are the same length. As the connector is moved relatively out of the outer tube/sleeve 4910, the recesses 5710 are simultaneously relatively moved out of the outer sleeve 4910. Since the extensions 5000 are all the same length, the recesses 5710 with the heads 5636 will all emerge from the delivery outer sleeve 4910 at the same time. Consequently, the heads 5636 of the docking station and/or doors 7020 will move radially outward and release all at once.

Figure 15A:
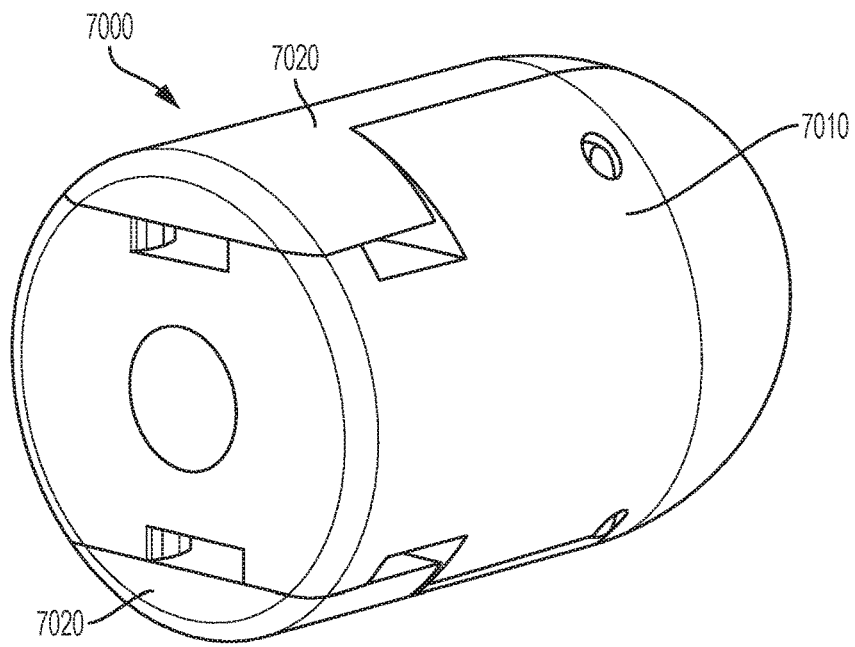
FIG. 15A is a perspective view of an exemplary embodiment of a lock and release connector in a closed position.
Figure 15B:
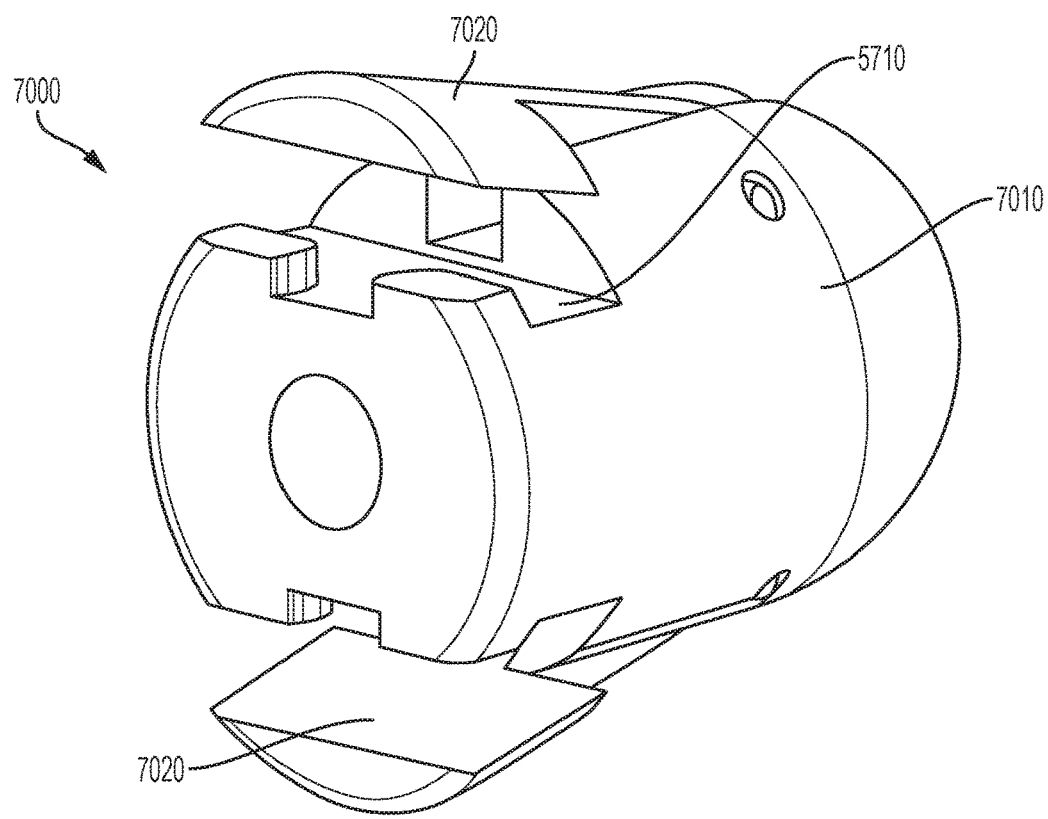
FIG. 15B is a perspective view of the exemplary lock and release connector of FIG. 15A in an open position.
Figure 16:
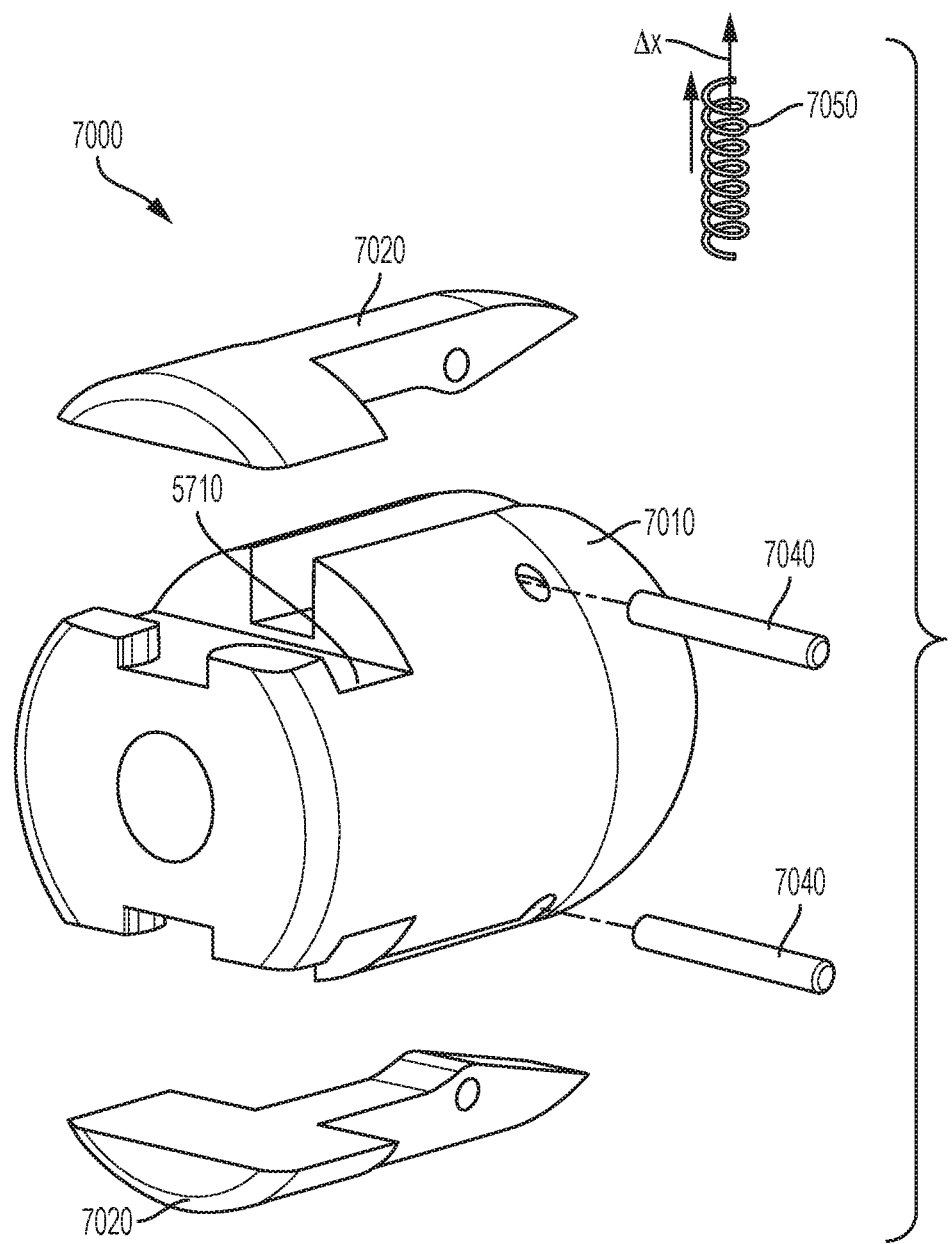
FIG. 16 is an exploded view of an exemplary embodiment of the lock and release connector.

FIG. 15A is a perspective view of one embodiment of a lock and release connector 7000 for a trans-catheter implantable device 10. The lock and release connector 7000 can be used to deploy the medical device 10 as illustrated in FIGS. 12A-12D. In one exemplary embodiment, a lock and release connector 7000 for a trans-catheter implantable device 10 comprises a body 7010 and at least one door 7020 engaged with the body 7010, wherein the door 7020 is moveable from a first position to a second position. In some exemplary embodiments, a first position can be a closed position, including without limitation a partially closed position. In other exemplary embodiments, a second position can be an open position, including without limitation a partially open position. In some exemplary embodiments, the door 7020 can be integral with the body 7010 (not shown). In some exemplary embodiments, the door 7020 can be connected to the body 7010. The lock and release connector 7000 can comprise a body 7010 and at least one door 7020 hingedly connected to the body 7010. In the illustrated embodiment, the lock and release connector has two doors 7020. However the lock and release connector 7000 can possess any number of doors, including without limitation, 1, 2, 1 to 2, 2 to 5, 3 to 4, 1 to 6 doors, or any other number of doors. Each door could be configured to hold/lock/retain a single extension 5000 or one or more doors (e.g., one or more doors 7020) could be configured to hold/lock/retain multiple extensions. FIG. 15A shows an exemplary embodiment of the lock and release connector 7000 wherein the doors 7020 are in a closed and/or first position. FIG. 15B illustrates a perspective view of the lock and release connector 7000 wherein the doors 7020 are in an open and/or second position. FIG. 16 is an exploded view of the lock and release connector 7000. In some embodiments, the lock and release connector 7000 can further include at least one fastener 7040 connecting at least one end of the door(s) 7020 to the body 7010. The body 7010 and the door(s) 7020 can be hingedly connected by a fastener 7040. In some embodiments, the fastener 7040 can be a hinge pin. The fastener 7040 can be a wire, a screw, hinge, suture, tie, latch, a pin, etc. The body 7010 and the door 7020 can be hingedly connected by any fastener known in the art.

In some exemplary embodiments the door 7020 is passively moved from the closed position to the open position. That is, in some embodiments, the lock and release connector 7000 does not include any mechanism that moves the doors 7020 to the open position from the closed position or to the closed position from the open position. For example, the doors 7020 can be forced open by an external force, such as the force of expansion of the stent, docking station or other medical device 10 when the device is deployed/released from the catheter.

In another exemplary embodiment, the door 7020 of the lock and release connector 7000 can optionally utilize a mechanism that causes the door 7020 to translate from a first position to a second position, including from a closed state to the open state and vice versa. In some exemplary embodiments, the door can be actively controlled to move from a first position to a second position. For example, the lock and release connector 7000 can further comprise at least one spring 7050 (or similar mechanism) exerting force on the door 7020 to bias the door open. In other examples, the door 7020 can be controlled by a control wire to translate the door 7020 from a first position to a second position, including from the closed state to the open state and vice versa. In some exemplary embodiments, the door 7020 can be made from shape memory or pseudo-elastic materials, such as shape-memory alloys, including without limitation, a copper-aluminum-nickel alloy, and a nickel-titanium alloy, one example of which includes nitinol. These shape memory materials allow the door 7020 to be compressed to a closed state to engage the body 7010, including without limitation a partially closed position, and then when the compression force is released (e.g., when deployed from the catheter), the door 7020 will self-expand back to its pre-compressed open state. In this embodiment, the illustrated fastener 7040 can be omitted. For example, the body 7010 and the door(s) 7020 can be integrally formed or fixed together and the door(s) 7020 can flex from a first position to a second position, including from a closed position to an open position.

Figure 17A:
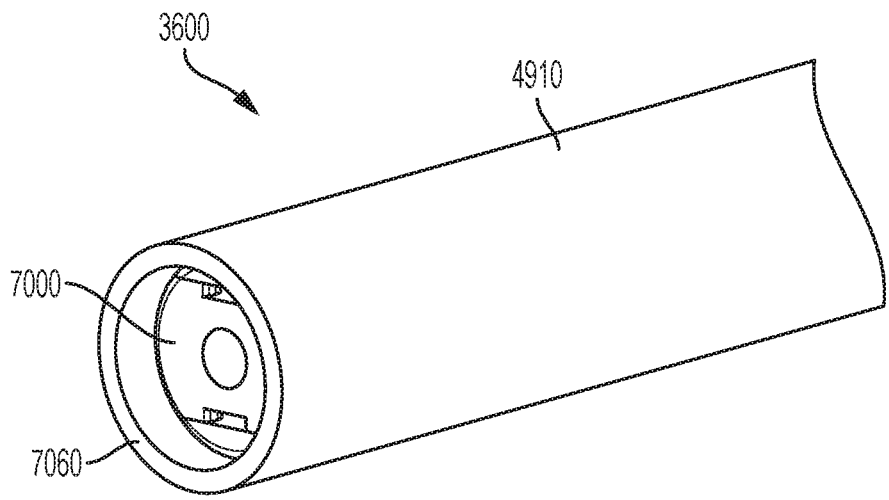
FIGS. 17A-21B are partial views of exemplary embodiments of a lock and release connector in various positions with respect to a catheter.
Figure 17B:
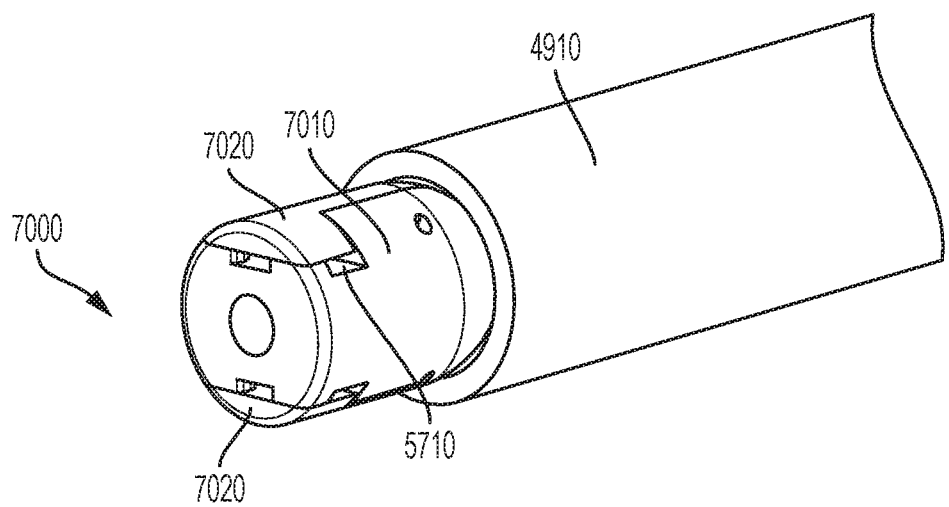

FIGS. 17A-17B illustrate a partial view of the catheter 3600 having an outer tube 4910 having a distal opening 7060. In the illustrated embodiment the connector 4914 is specifically the lock and release connector 7000 having a body 7010 and a door 7020 connected to the body 7010. The lock and release connector 7000 can be used to retain an implantable medical device 10 in the delivery catheter 3600 until the medical device is moved relatively out of the catheter 3600 or outer tube/sleeve/sheath 4910 (e.g., by retracting the outer tube/sleeve/sheath 4910 or by advancing the lock and release connector 7000).

Figure 11A:
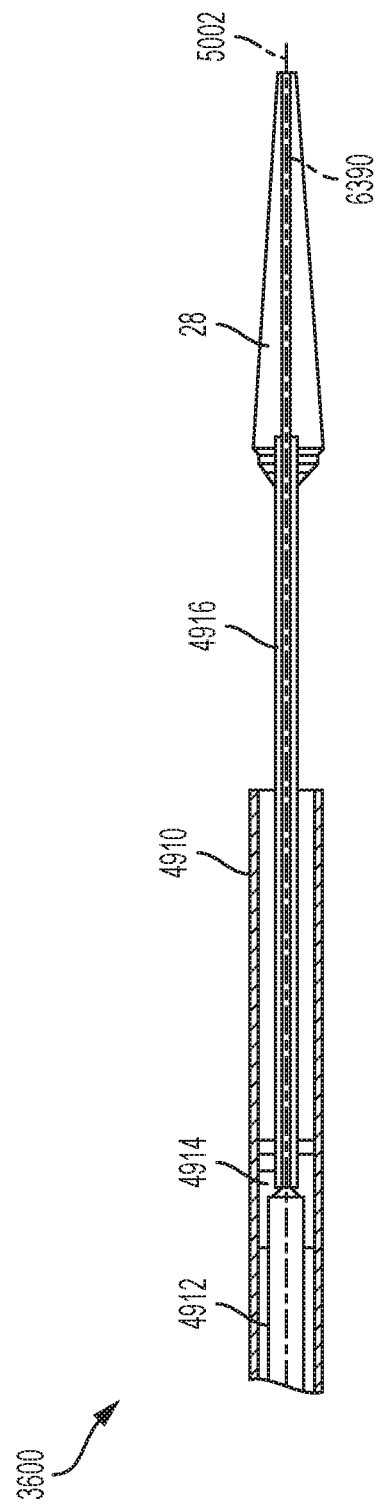
FIG. 11A is a sectional view of an exemplary embodiment of a catheter.
Figure 11B:
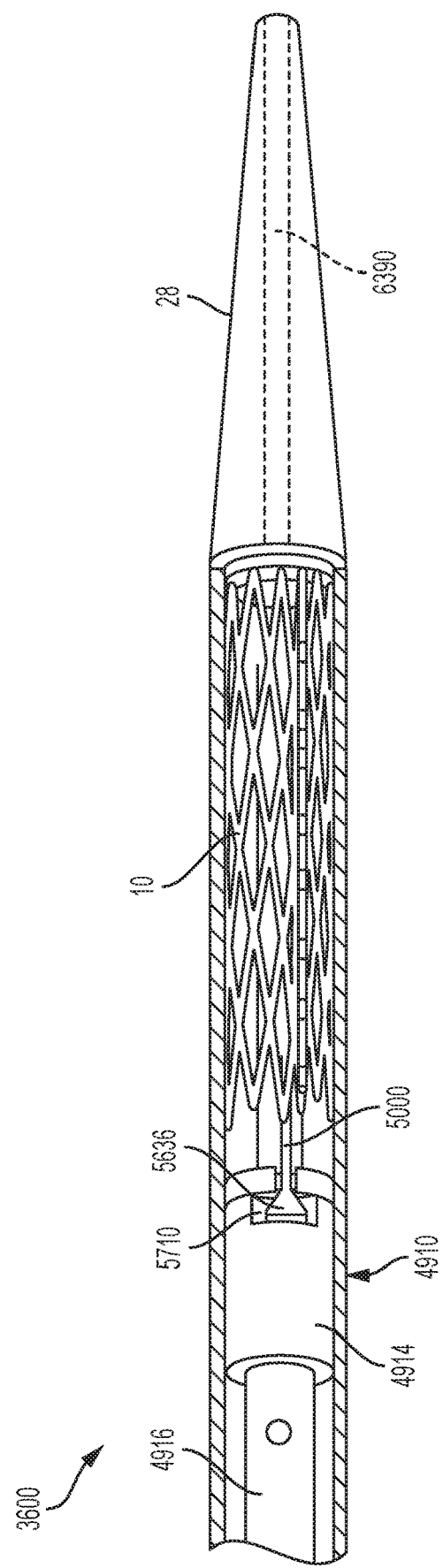
FIG. 11B is a sectional view of an exemplary embodiment of a catheter with an exemplary implantable medical device crimped and loaded in the catheter.
Figure 18A:
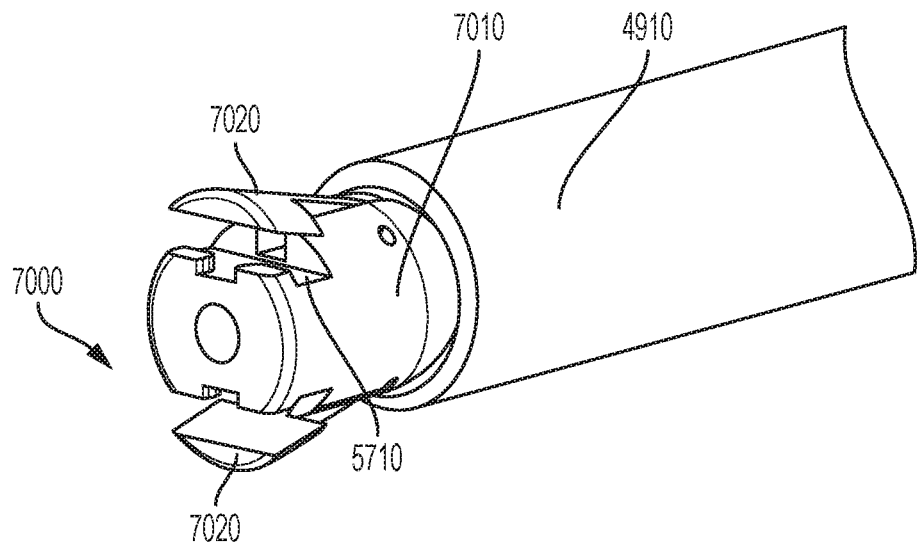

In some exemplary embodiments, the lock and release connector 7000 is connected to the inner tube 4912 in a manner similar to the connector 4914 (See FIG. 11B). FIGS. 18A-21B illustrate one manner in which one or more extension 5000 of an implantable medical device 10 are placed between the body 7010 and the door 7020 of the lock and release connector 7000. Referring to FIG. 18A, outer tube 4910 is progressively retracted with respect to the lock and release connector 7000, which allows the door 7020 to reach the open position. Alternatively, the lock and release connector 7000 can be progressively advanced with respect to the outer tube 4910 to allow the door 7020 to reach the open and/or second position.

The door 7020 can be passive and opened by extensions 5000 of a medical device or reach the open and/or second position using a variety of active mechanisms. In the passive embodiments, the door is opened or is translate to a second position by the release of the potential energy stored in the implantable device or "stent" itself, when the outer tube 4910 is retracted.

Figure 27:
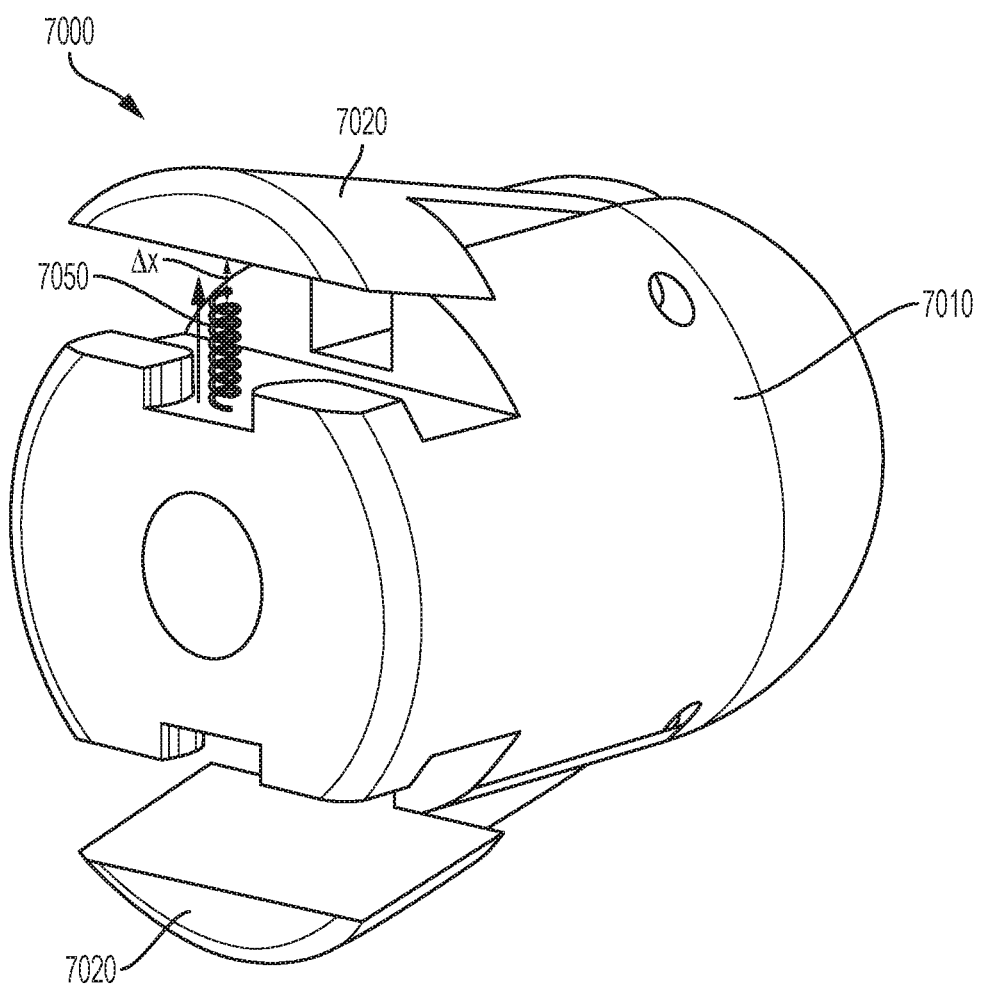
FIG. 27 is a perspective view of an exemplary embodiment of a lock and release connector.

In some embodiments, the resting state of the door 7020 is in the open and/or second position so that the door 7020 changes position passively when the outer tube 4910 is retracted. In some embodiments, the door 7020 opens or translates to a second position by releasing the potential energy stored in a spring 7050 placed between the door 7020 and the body 7010 (shown schematically in FIG. 27). In some embodiments, the door 7020 can be controlled by a control wire or guidewire 5002 to translate the door 7020 from a first position to a second position, including from the closed state to the open state and vice versa. In some embodiments, the door 7020 is configured from shape memory materials, such as a nickel titanium alloy like nitinol. These shape memory materials allow the door 7020 to be compressed to a closed state when confined inside the outer tube 4910, and then when the compression force is released, the door 7020 will self-expand back to its pre-compressed open state. In this embodiment, the illustrated moveable connection between the door 7020 and the body 7010 can be omitted. The door(s) can be fixedly attached to the body and flex from the closed position to the open position.

Figure 18B:
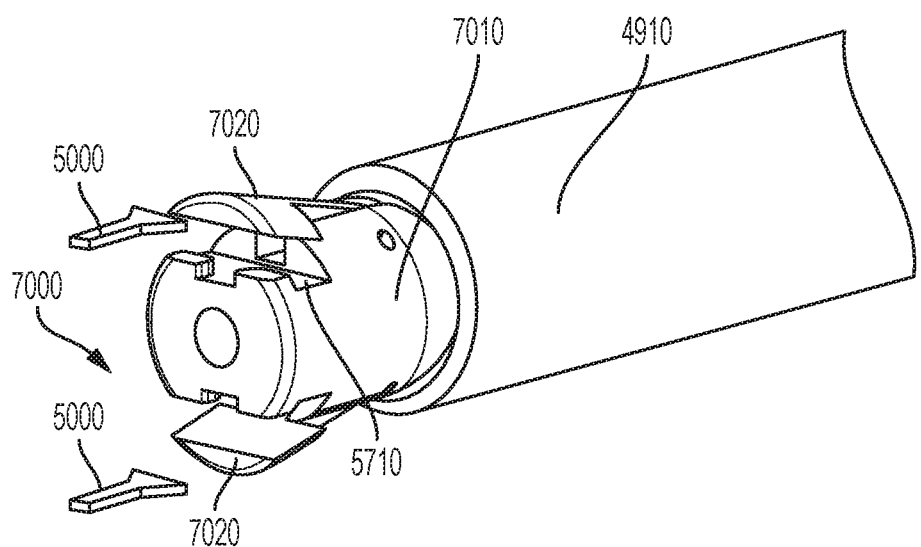
Figure 19A:
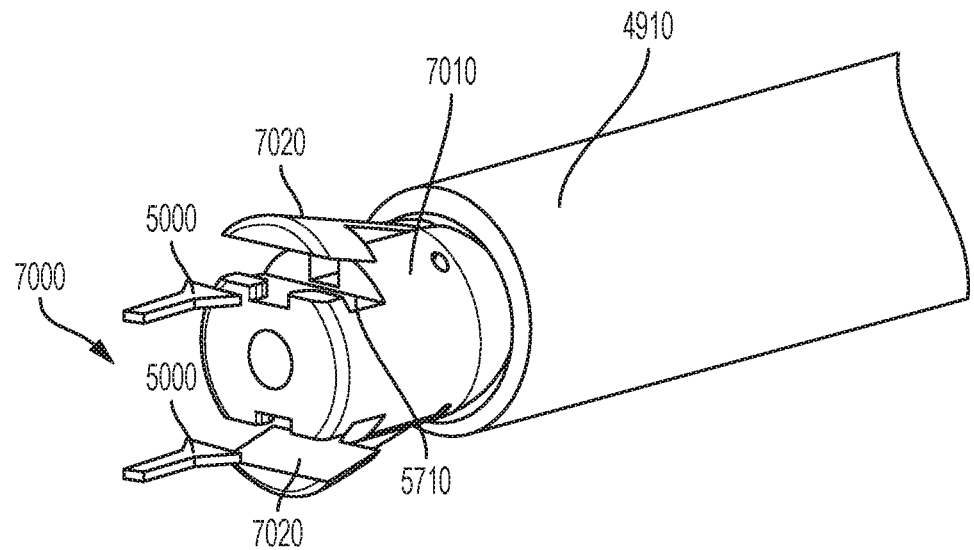
Figure 19B:
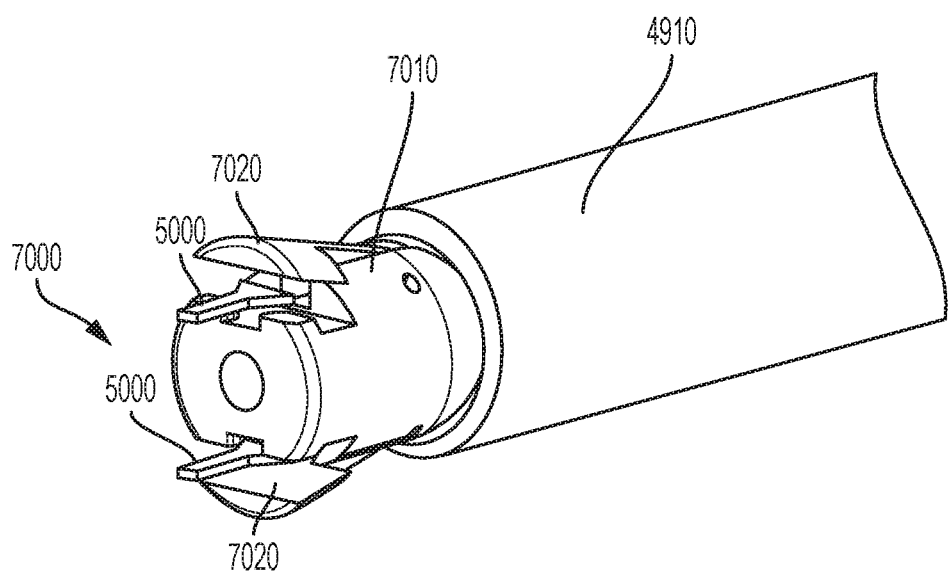
Figure 20A:
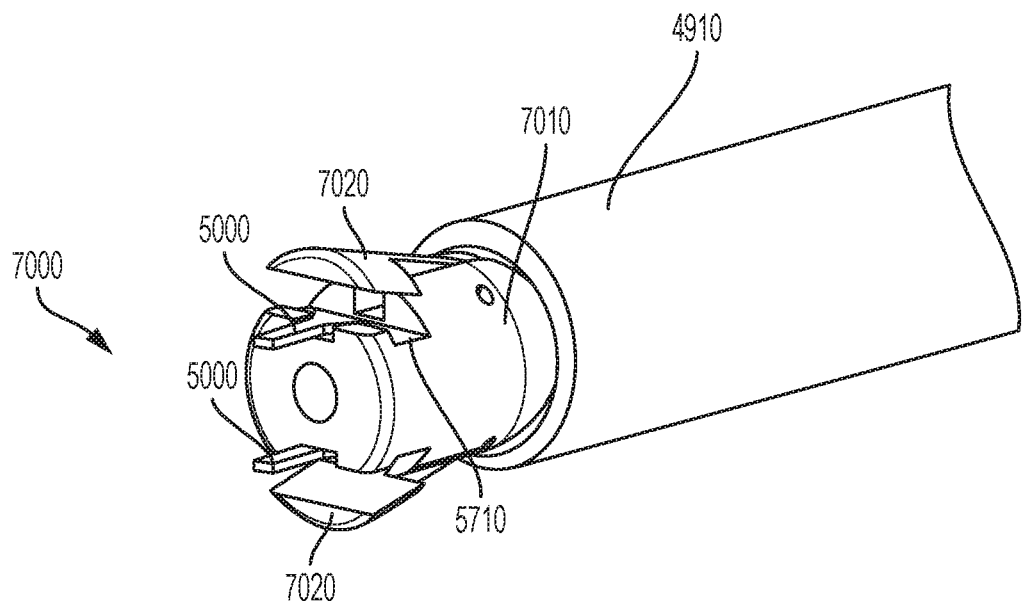
Figure 20B:
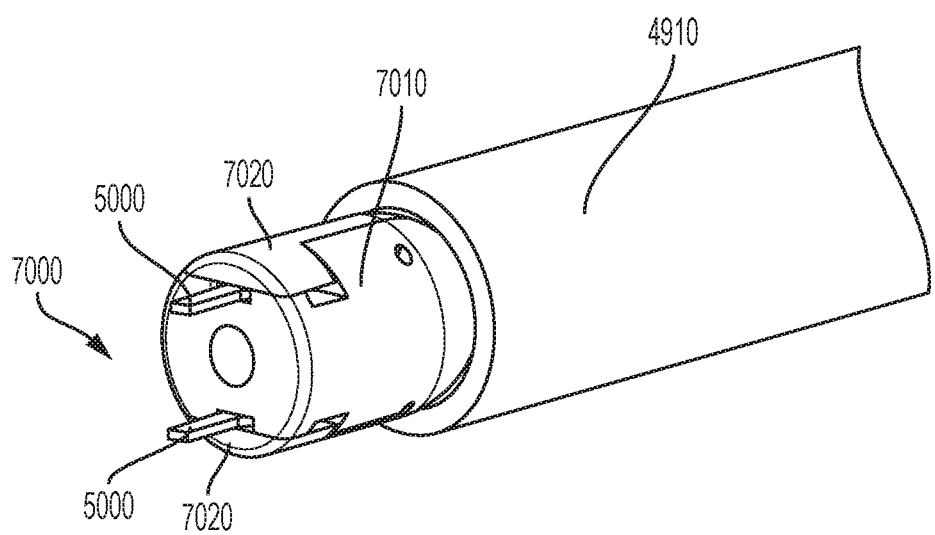

As shown in FIGS. 18B-20B, to connect the implantable medical device 10 (See for example FIGS. 9 and 11B) to the lock and release connector 7000, the extensions 5000 are interposed between the body 7010 and the door 7020 of the lock and release connector 7000. As shown in FIG. 18B, the extensions 5000 are brought into proximity with the lock and release mechanism 7000. In FIG. 19A, the extensions 5000 are compressed toward one another. In FIG. 19B, the extension 5000 are moved into the spaces between the doors 7020 and the body 7010. FIG. 20A illustrates the extension 5000 being placed in a cutout or recess 5710 in the body 7010. FIG. 20B illustrates the doors 7020 being closed to connect the implantable medical device to the lock and release connector. The doors 7020 can be closed as illustrated by FIG. 20 when the doors are controlled by a control wire (not shown) that is connected to the door and extends through the catheter 3600, to the proximal end of the catheter. However, the doors 7020 can be closed by merely advancing the outer tube/sleeve/sheath 4910 over the lock and release connector 7000 or by retracting the lock and release device 7000 into the outer tube 4910 of the catheter. That is, the distal opening 7060 or outer surface of the outer tube 4910 engages the doors 7020 to close the doors as the lock and release device is covered by the tube 4910.

Figure 21A:
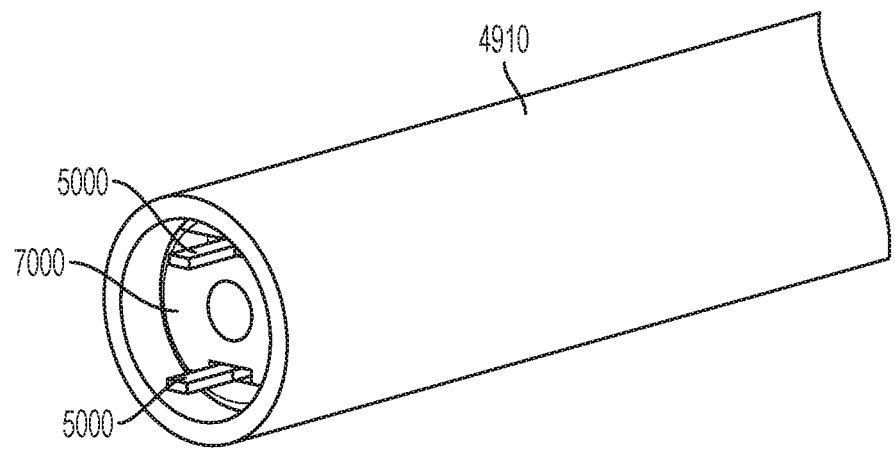
Figure 21B:
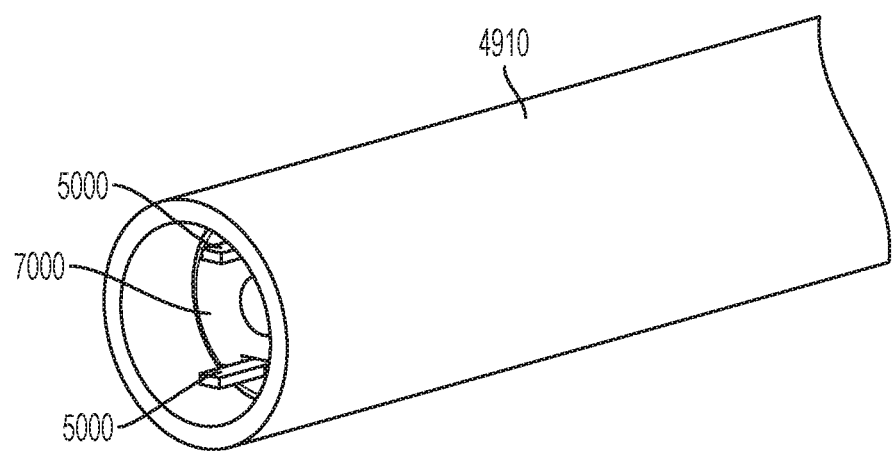
Figure 22:
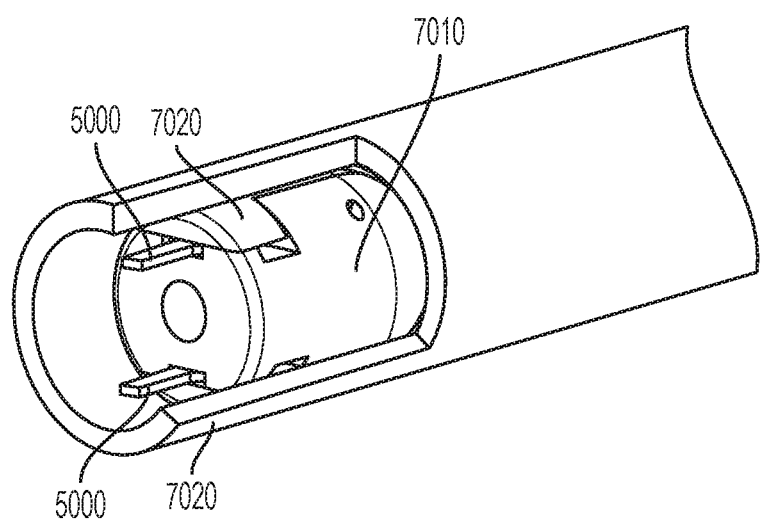
FIGS. 22-23 are cut-away partial views of exemplary embodiments of a lock and release connector and the catheter.
Figure 23:
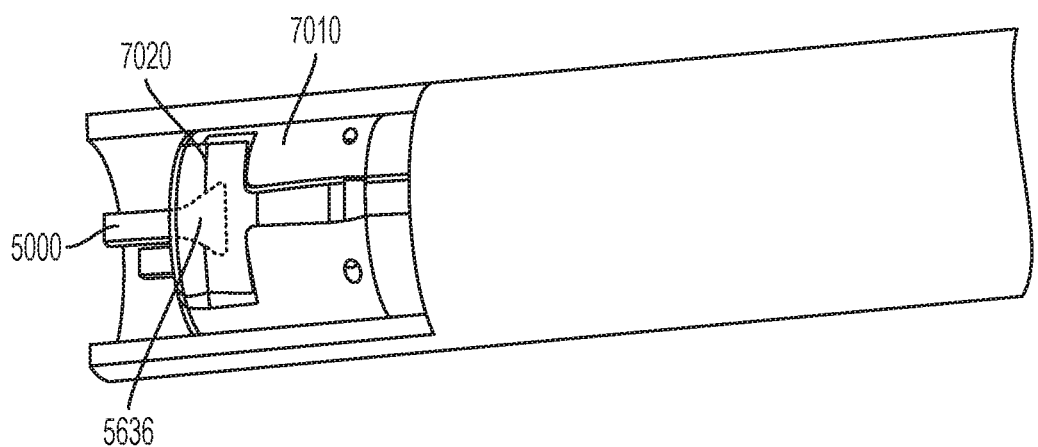

As illustrated in FIGS. 21A-21B, once the extensions have been placed, the outer tube 4910 is advanced (or the lock and release device 7000 is retracted) to cover the lock and release connector 7000 until each door 7020 closes to lock each extension 5000 in place into the cutout or recess 5710. FIGS. 22-23 are cut-away views showing the lock and release connector 7000 inside the outer tube 4910 wherein the door 7020 is in the closed and/or first position having the extensions locked in place. The heads 5636 of each extension 5000 fit into the T-shaped recesses 5710 in the lock and release device 7000 to hold the proximal end 12 of the medical device 10. When the outer tube/sleeve 4910 of the catheter 3600 is closely disposed over the lock and release connector 7000, the heads 5636 are captured in the recesses 5710, between the body 7010 and the door 7020. This capturing in the recesses 5710 holds the end of the medical device 10 as the medical device expands. In this manner, delivery of the medical device 10 is controlled. When the device 10 is partially deployed, the device 10 can also be recaptured by advancing the outer tube/sheath over the device 10 again or retracting the device 10 into the outer tube/sheath.

Figure 24A:
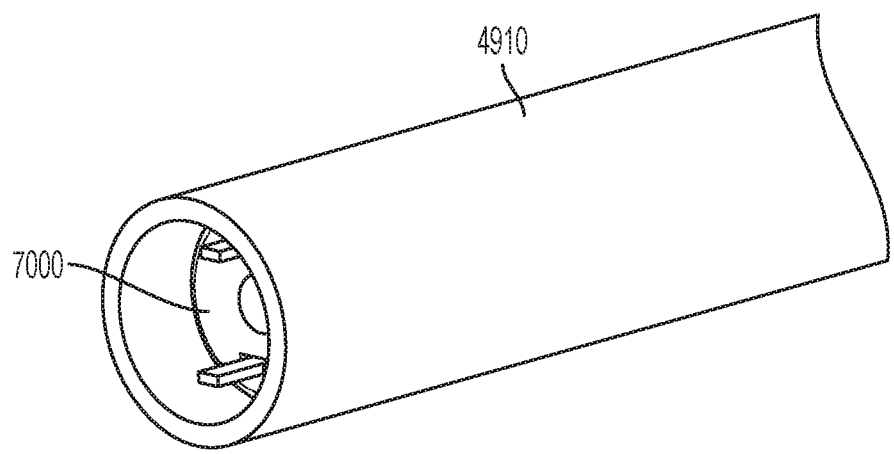
FIGS. 24A-25B are partial views of exemplary embodiments of a lock and release connector deploying the extensions and being retracted into the catheter.
Figure 24B:
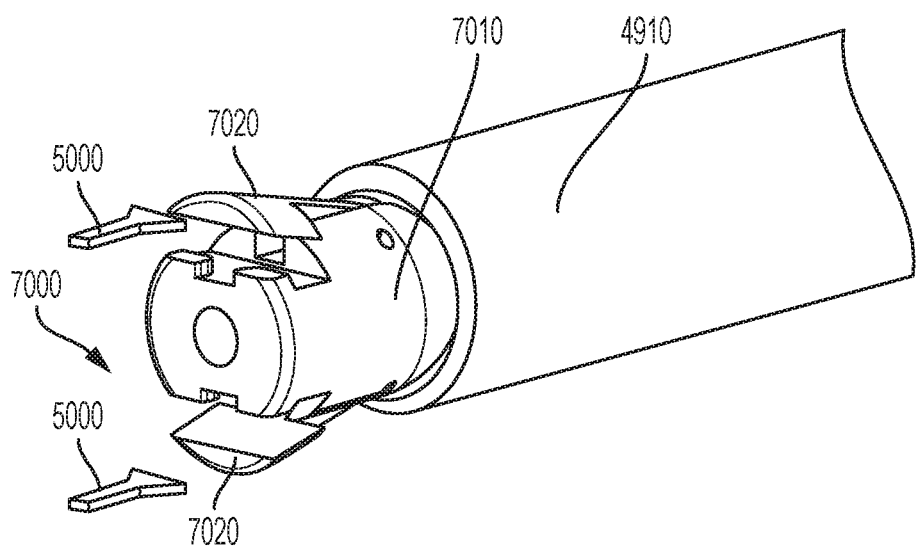
Figure 25A:
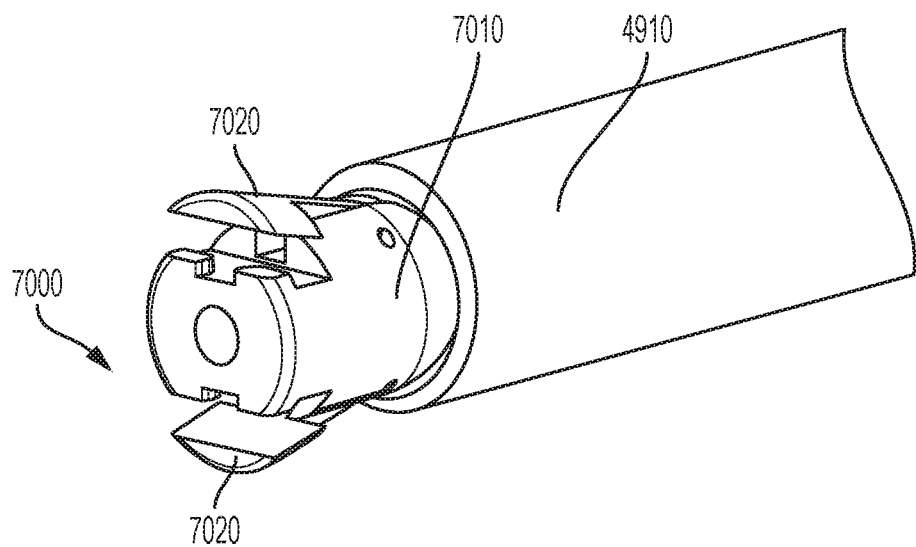
Figure 25B:
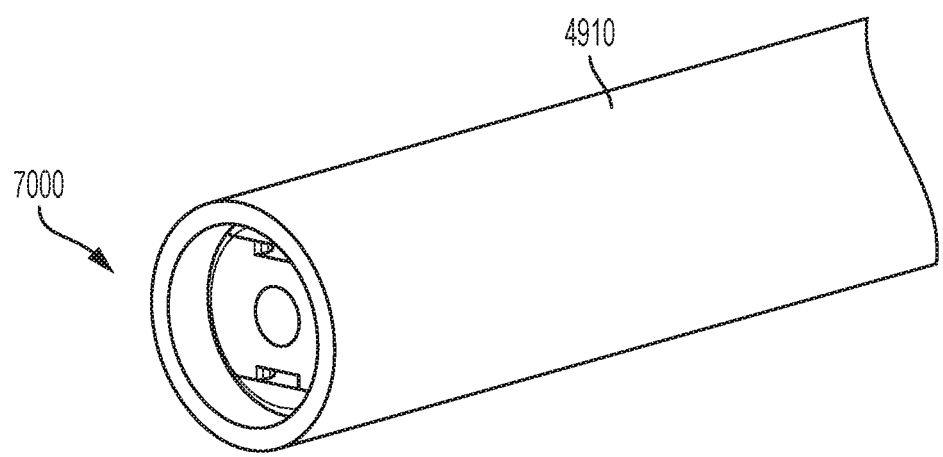

FIGS. 24A-25B illustrate an exemplary embodiment of release of the extensions 5000 of the implantable medical device 10 from between the body 7010 and the door 7020 of the lock and release connector 7000. Referring to FIGS. 24A-24B, outer tube 4910 is progressively retracted with respect to the lock and release connector 7000, which allows the door 7020 to reach the open and/or second position. Optionally, the lock and release connector 7000 can be progressively advanced with respect to the outer tube 4910 to allow the door 7020 to reach the open and/or second position, or the lock and release connector 7000 can be advanced simultaneously with retraction of the outer tube/sheath. Once the door 7020 opens the extensions 5000 are released. For example, the potential energy stored in the extensions 5000 can force the doors 7020 open and cause the extensions to expand outward, out of the doors. Referring to FIGS. 25A-25B, as the outer tube 4910 is advanced over the lock and release connector 7000, the door 7020 is pressed to the closed and/or first position by the outer tube 4910.

Figure 26A:
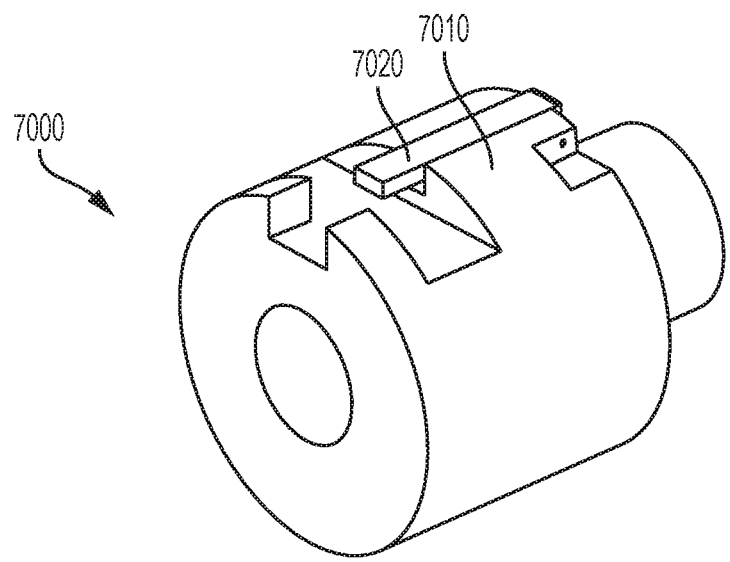
FIGS. 26A-26B are perspective views of exemplary embodiments of a lock and release connector.
Figure 26B:
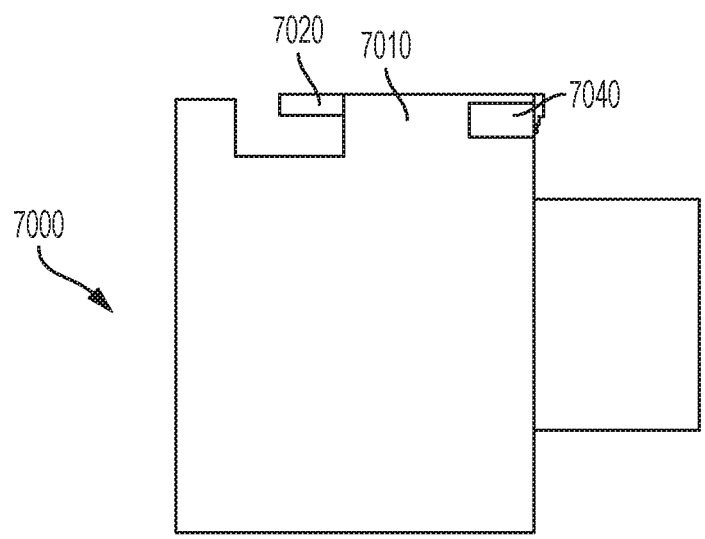

FIGS. 26A-26B illustrate another embodiment of the lock and release connector 7000 where the door 7020 is simplified and minimized. In this example, the door 7020 has a small, simple rectangular shape. However, the door 7020 can have any shape including, without limitation, t-shaped, triangular, octagonal, square, cylindrical, or any other shape adapted to retain the extension 5000 in the lock and release connector 7000.

The lock and release connector 7000 can be configured to allow the medical device to be retrieved or retracted back into the catheter assembly after partial deployment, e.g., when the outer tube 4910 is advanced enough to expose a portion of the medical device but still prevent the lock and release connector 7000 from releasing the extensions 5000. For example, 30%-90% of the length of the implantable medical device 10 (or any range between 30% and 90%, including without limitation 20%-80%, 30%-60%, 40%-90%, 60%-40%, 50%-80%, etc.) may be exposed from the outer tube 4910 while the doors 7020 still retain the implantable medical device 10 and allow the implantable medical device 10 to be pulled back into the tube 4910. If the lock and release connector 7000 is prevented from releasing the extensions 5000, then the implantable medical device 10 can be retracted back into the catheter to reposition the catheter before redeployment of the medical device, thus allowing the medical device to be recovered and repositioned after partial deployment.

As mentioned above, the lock and release connector 7000 can be used to controllably deploy a wide variety of different medical devices in a wide variety of different applications. The human heart H is one of the many places where the lock and release connector 7000 can be used. The lock and release connectors 7000 can be used to deploy a wide variety of different devices in the heart. Some details of the human heart and a docking station for providing a landing zone are described below to provide an example of one of the many applications where the connector 7000 can be used.

Referring back to FIGS. 1A and 1B, the human heart H is illustrated in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta (not identified) and the pulmonary valve PV separates the right ventricle from the pulmonary artery PA. Each of these valves has flexible leaflets extending inward across the respective orifices that come together or "coapt" in the flowstream to form the one-way, fluid-occluding surfaces.

The right atrium RA receives deoxygenated blood from the venous system through the superior vena cava SVC and the inferior vena cava IVC, the former entering the right atrium from above, and the latter from below. The coronary sinus CS is a collection of veins joined together to form a large vessel that collects deoxygenated blood from the heart muscle (myocardium), and delivers it to the right atrium RA. During the diastolic phase, or diastole, seen in FIG. 1A, the venous blood that collects in the right atrium RA passes through the tricuspid valve TV as the right ventricle RV expands. In the systolic phase, or systole, seen in FIG. 1B, the right ventricle RV contracts to force the venous blood through the pulmonary valve PV and pulmonary artery into the lungs. During systole, the leaflets of the tricuspid valve TV close to prevent the venous blood from regurgitating back into the right atrium RA.

As mentioned above, the lock and release connector can be used to retain and release a wide variety of different implantable medical devices. Referring to FIGS. 2A-2B, in one exemplary embodiment an implantable medical device 10 is depicted as an expandable docking station that includes one or more sealing portions 410, a valve seat 18, and one or more retaining portions 414. The sealing portion(s) 410 provide a seal between the medical device 10 and an interior surface 416 of the circulatory system. The valve seat 18 provides a supporting surface that can be used mounting a valve in the device 10 or for implanting or deploying a valve (e.g., a THV) in the device 10 (configured as a docking station) after the device/docking station is implanted in the circulatory system. The retaining portions 414 can help retain the medical device 10 (e.g., docking station) and the valve at the implantation position or deployment site in the circulatory system. The expandable docking station(s) as described or shown in various embodiments herein are also representative of a variety of docking stations, valves, and/or other medical devices 10 that might be known or developed.

FIGS. 2A-2B schematically illustrate an exemplary deployment of the medical device 10. In some exemplary embodiments, the medical device is in a compressed form/configuration and is introduced to the deployment site in the circulatory system. For example, the medical device 10, can be positioned at a deployment site in a pulmonary artery by a catheter (e.g., catheter 3600 as shown in FIGS. 12A-12D). Referring to FIG. 2B, the medical device 10 is expanded in the circulatory system such that the sealing portion(s) 410 and the retaining portions 414 engage the inside surface 416 of a portion of the circulatory system.

The medical device can be made from a highly flexible metal, metal alloy, or a polymer. Examples of metals and metal alloys that can be used include, but are not limited to, nitinol, elgiloy, and stainless steel, but other metals and highly resilient or compliant non-metal materials can be used. For example, the medical device 10 can have a frame or portion of a frame (e.g., a self-expanding frame, retaining portion(s), sealing portion(s), valve seat, etc.) made of these materials, e.g., from shape memory materials, such as nitinol. These materials allow the frame to be compressed to a small size, and then when the compression force is released, the frame will self-expand back to its pre-compressed diameter.

Figure 3:
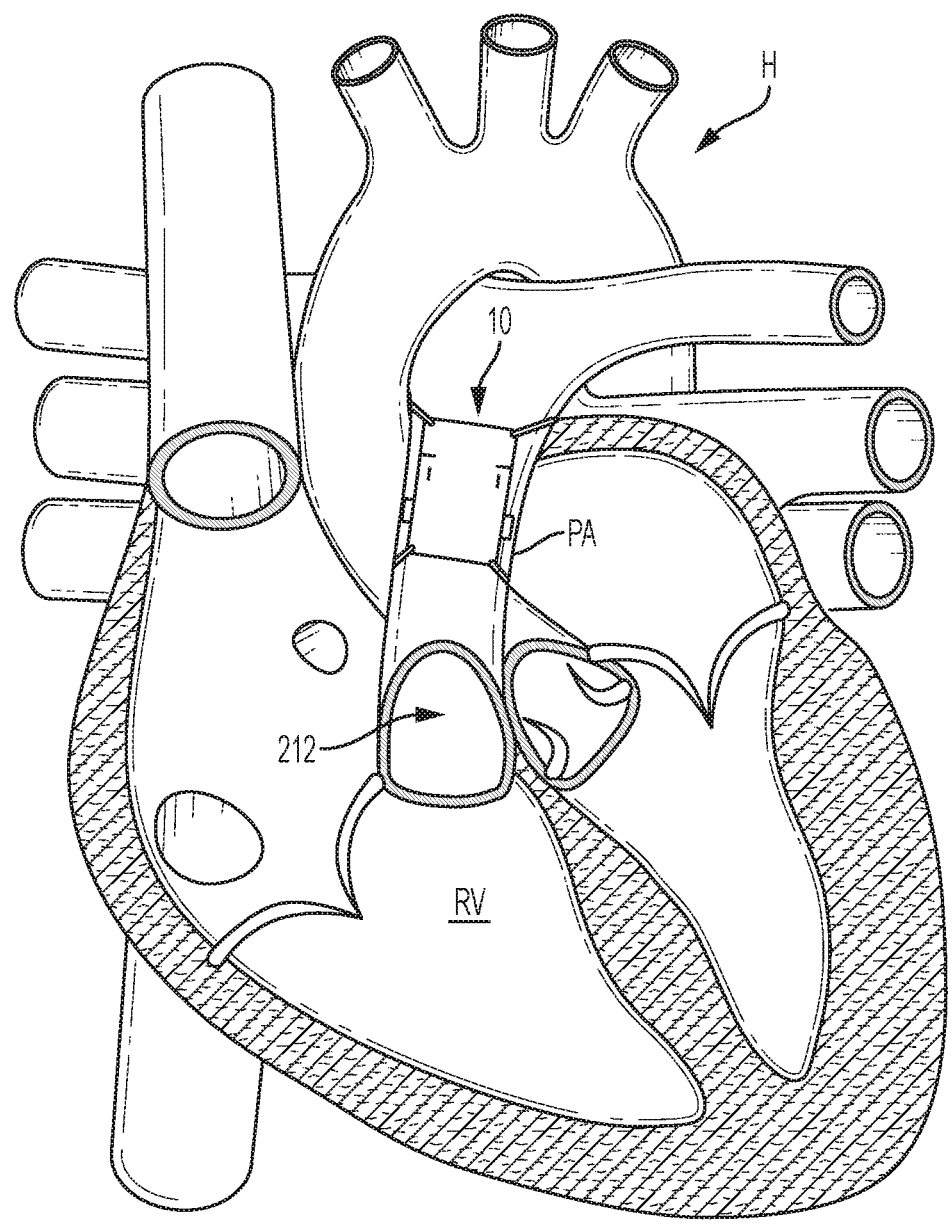
FIG. 3 is a cutaway view of the human heart in a systolic phase with a medical device deployed in a pulmonary artery.
Figure 4:
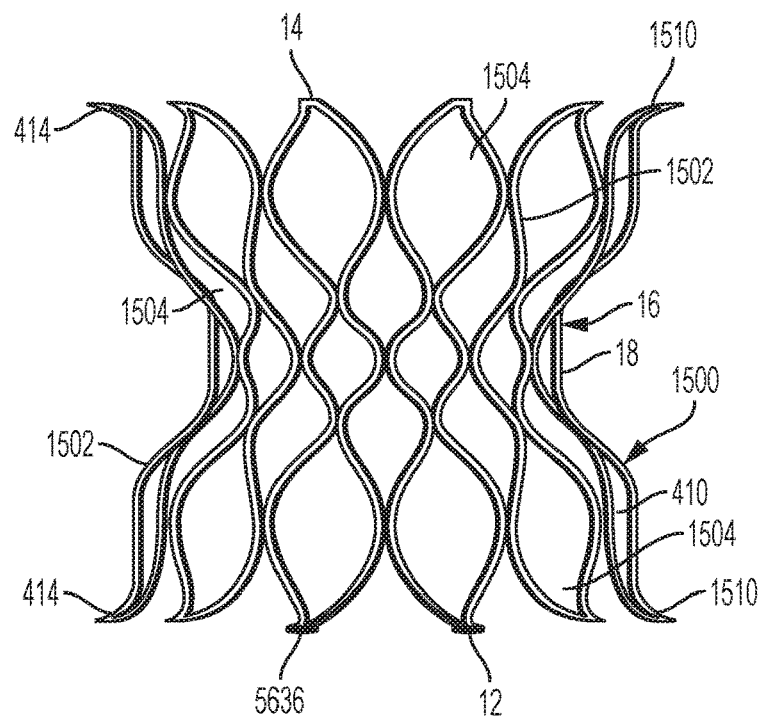
FIG. 4 is a side view of an exemplary embodiment of a frame of an implantable medical device.
Figure 5:
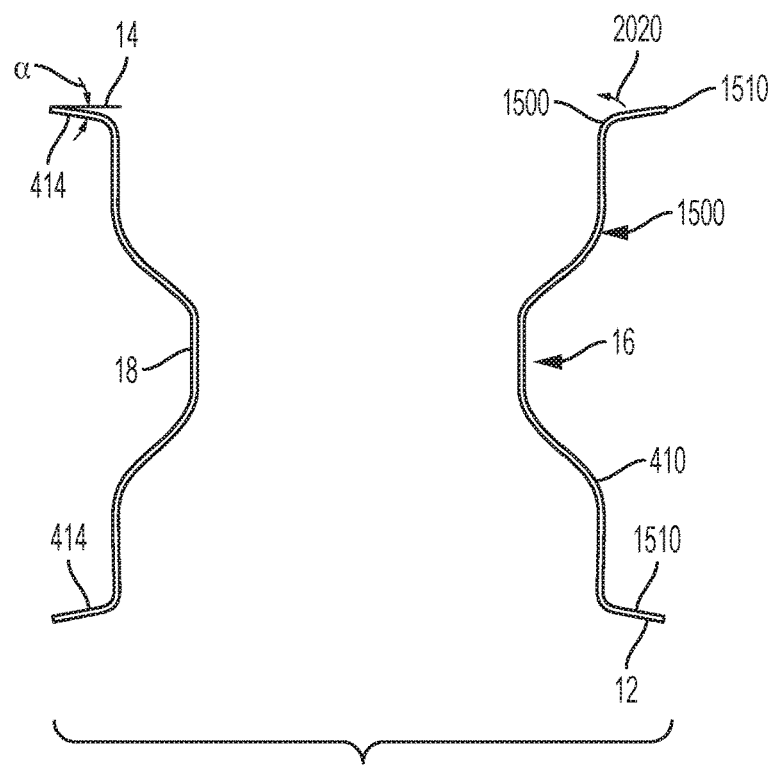
FIG. 5 illustrates a side profile of the frame illustrated by FIG. 4.

Referring to FIG. 3, the medical device 10 is shown, for example, retained in the pulmonary artery PA by expanding one or more of the retaining portions 414 radially outward into an area of the pulmonary artery PA. For example, the retaining portions 414 can be configured to extend radially outward into the pulmonary bifurcation 210 and/or the opening 212 of the pulmonary artery to the right ventricle.

FIGS. 4-8 illustrate an exemplary embodiment of a frame 1500 or body of an implantable medical device 10 (e.g., a docking station, stent, stent-graft, THV, etc.). The frame 1500 or body can take a wide variety of different forms and FIGS. 4, 5, 6, 7, and 8 illustrate just one of the many possible configurations. The device 10 has a relatively wider proximal inflow end 12 and distal outflow end 14, and a relatively narrower portion 16 that forms the seat 18 (e.g., can be used for mounting/attaching or docking a valve therein) in between the ends 12, 14. In the examples illustrated by FIGS. 4, 5, 7, and 8, the frame 1500 of the device 10 is depicted as a stent comprised of a plurality of metal struts 1502 that form cells 1504. In the example of FIGS. 4, 5, and 7-10, the frame 1500 has a generally hourglass-shape that has a narrow portion 16, which forms the valve seat 18 and is covered by a covering/material 21, in between the proximal and distal ends 12, 14.

Figure 6:
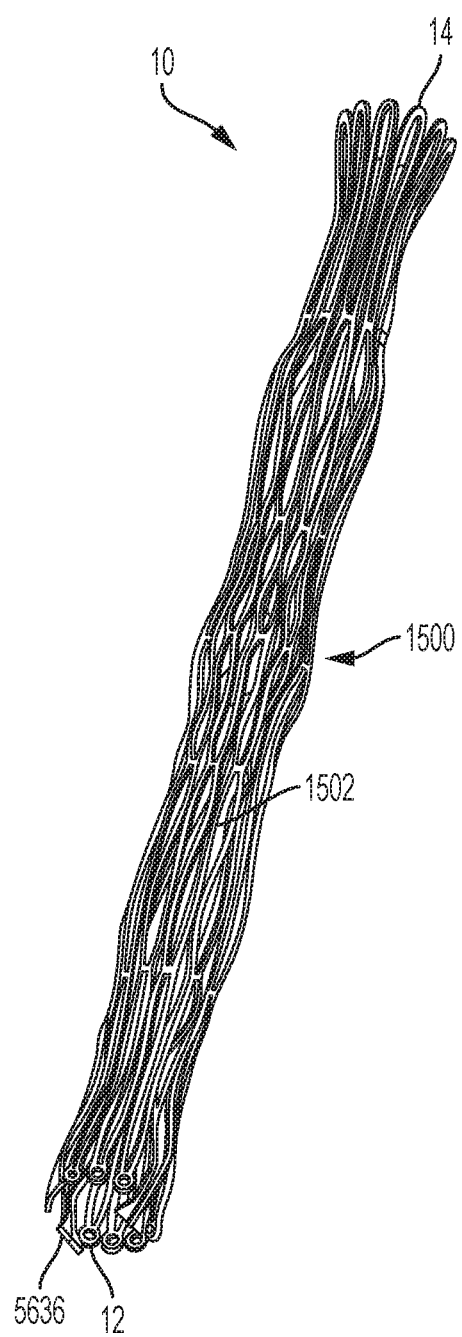
FIG. 6 illustrates the frame of FIG. 4 in a compressed state.
Figure 7:
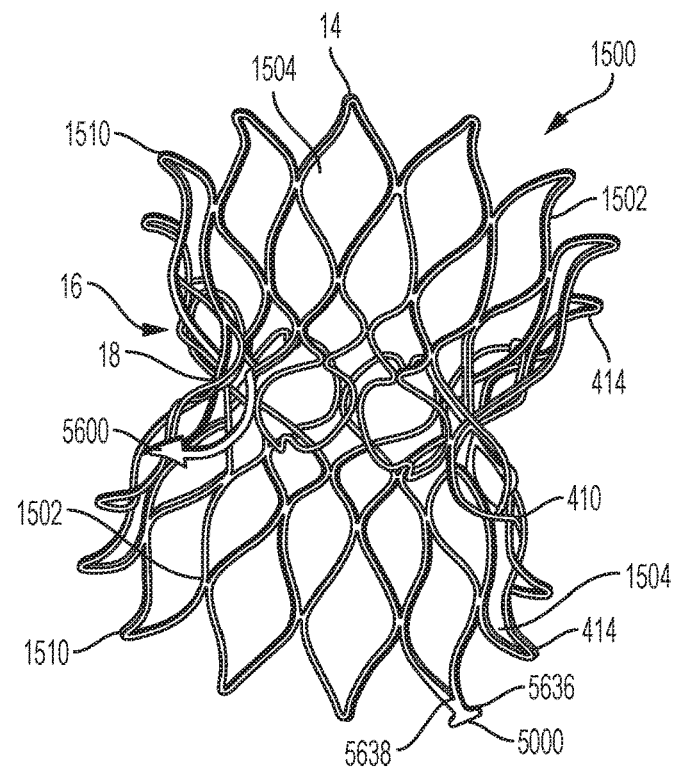
FIG. 7 is a perspective view of the frame of FIG. 4.
Figure 8:
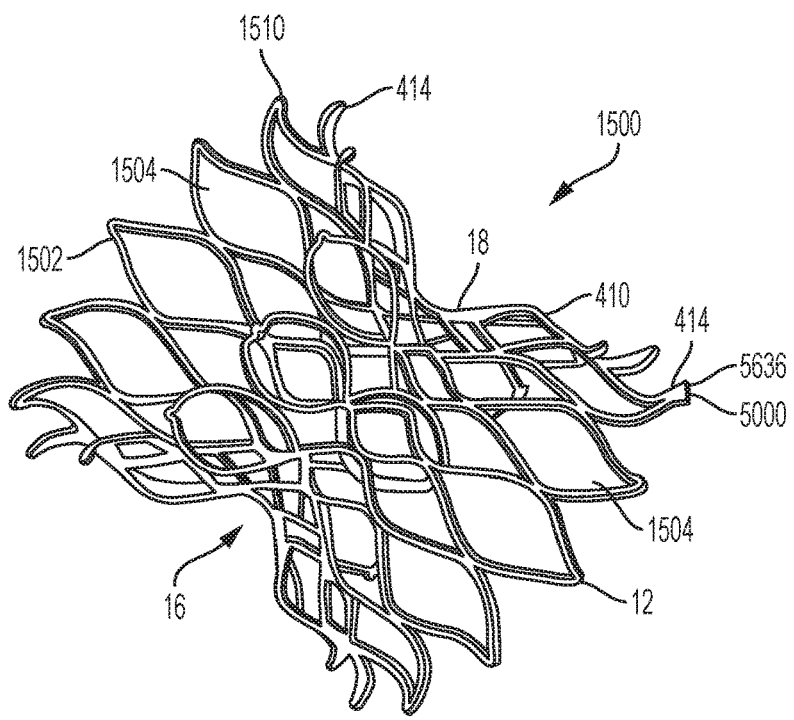
FIG. 8 is a perspective view of the frame of FIG. 4.

FIGS. 4, 5, 7, and 8, illustrate the frame 1500 in its unconstrained, expanded condition/configuration. In this exemplary embodiment, the retaining portions 414 comprise ends 1510 of the metal struts 1502 at the proximal and distal ends 12, 14. The sealing portion 410 is shown between the retaining portions 414 and the waist 16. In the unconstrained condition, the retaining portions 414 extend generally radially outward and are radially outward of the sealing portion 410. FIG. 6 illustrates the frame 1500 in the compressed state for delivery and expansion by a catheter. The device 10 can be made from a very resilient or compliant material to accommodate large variations in the anatomy. For example, the docking station can be made from a highly flexible metal, metal alloy, and/or polymer. An example of a highly resilient metal is nitinol, but other metals and highly resilient or compliant non-metal materials can be used. The device 10 can be self expandable, manually expandable (e.g., expandable using balloon), mechanically expandable, or a combination of these.

Figure 9:
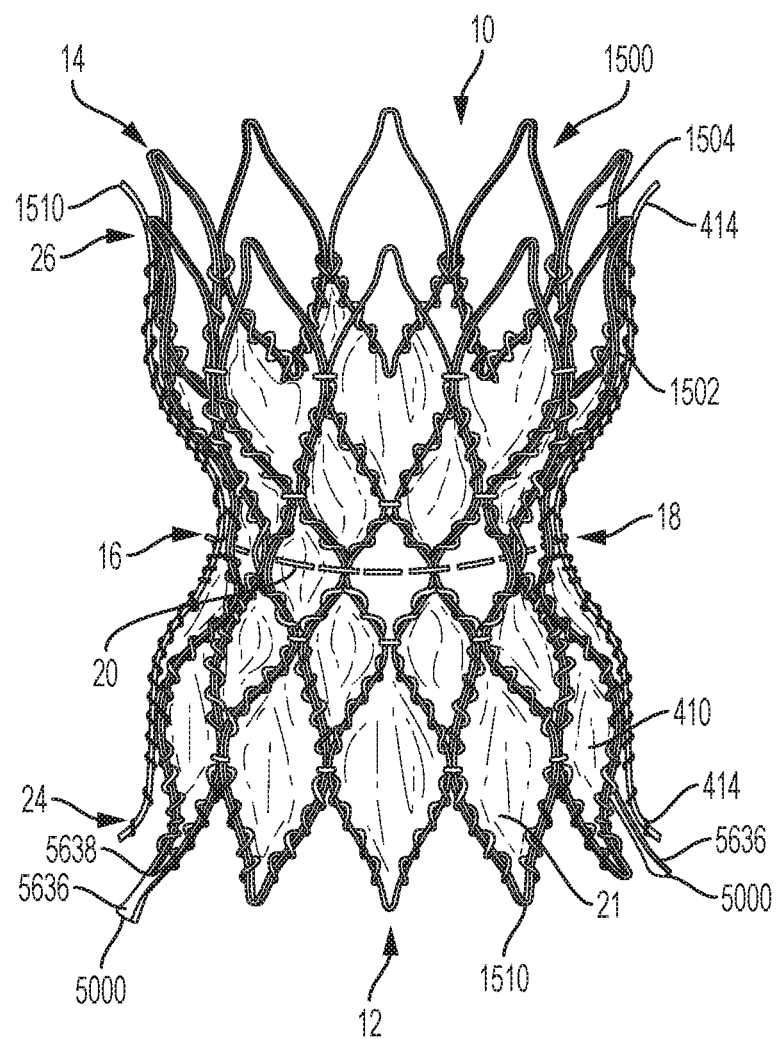
FIG. 9 is a perspective view of an exemplary embodiment of a covered frame of an implantable medical device having a plurality of covered cells and a plurality of open cells.
Figure 9A:
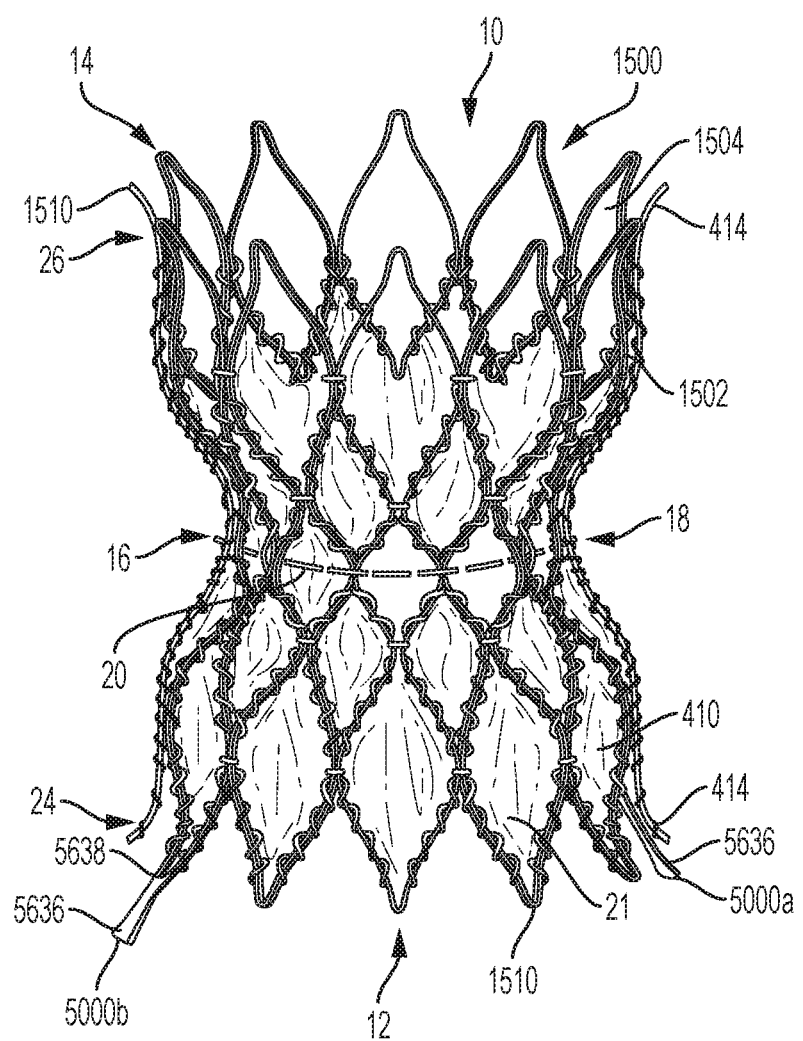
FIG. 9A is a perspective view of an exemplary embodiment of a covered frame of an implantable medical device having a plurality of covered cells and a plurality of open cells.
Figure 9B:
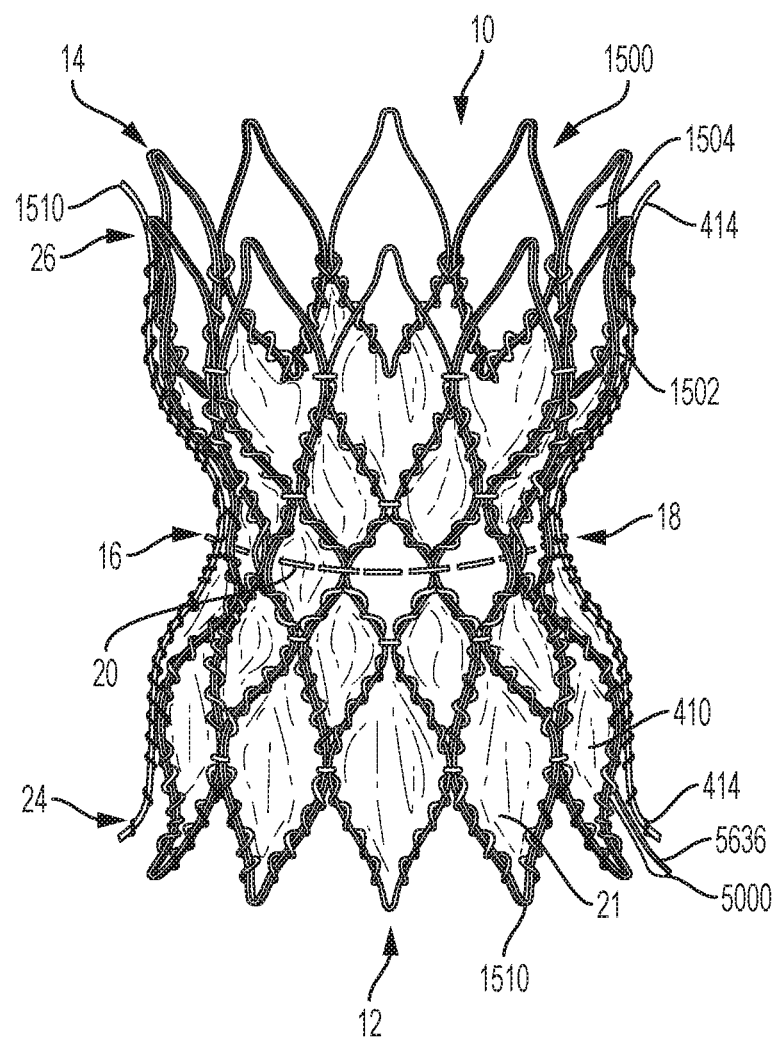
FIG. 9B is a perspective view of an exemplary embodiment of a covered frame of an implantable medical device having a plurality of covered cells and a plurality of open cells.

FIGS. 9, 9A, and 9B illustrate a frame 1500 with a covering/material 21 (e.g., an impermeable or semi-permeable material) attached to the frame 1500. A band 20 can extend about the waist or narrow portion 16, or can be integral to the waist to form an unexpandable or substantially unexpandable valve seat 18. The band 20 can stiffen the waist and, once deployed as a docking station is deployed and expanded, can make the waist/valve seat unexpandable or relatively unexpandable in its deployed configuration.

Figure 10:
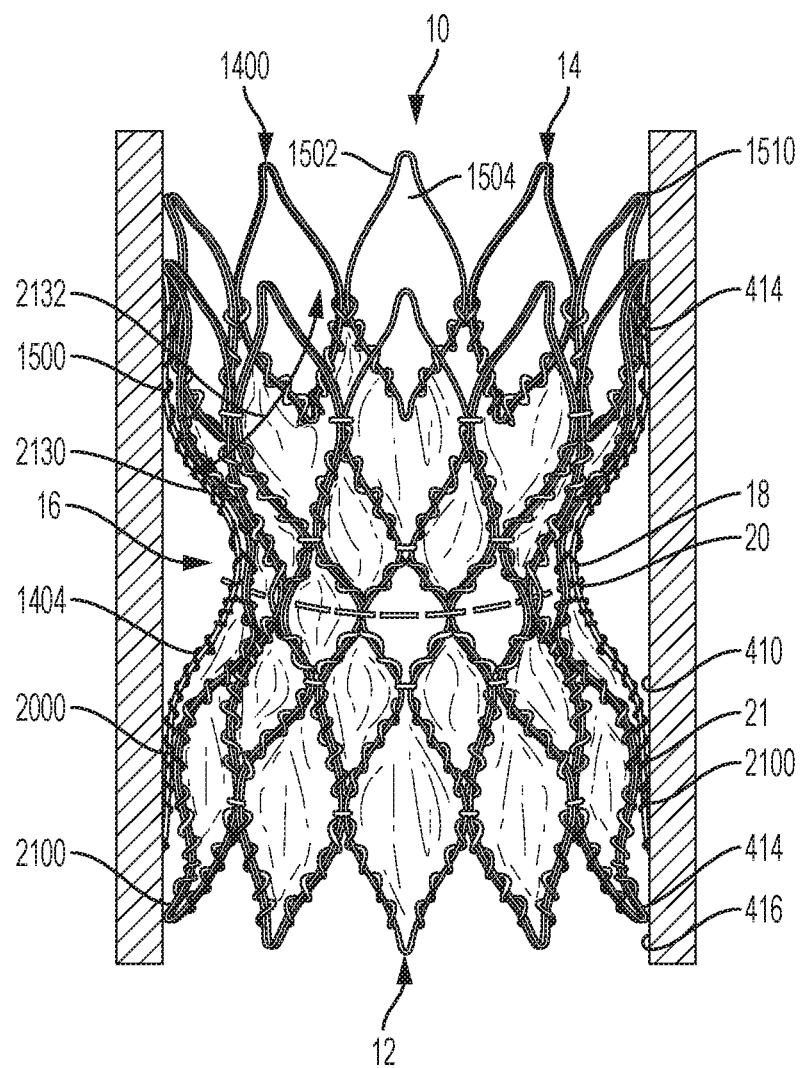
FIG. 10 illustrates a perspective view of the covered frame illustrated by FIG. 9 when installed in a vessel of the circulatory system.

FIG. 10 illustrates the implantable device 10 of FIG. 9 after being implanted in the circulatory system (e.g., in the pulmonary artery, IVC, SVC, aorta, etc.) using the connector 4914, such as the lock and release connector 7000. The sealing portions 410 provide a seal between the device 10 and an interior surface 416 of the circulatory system. The sealing portion 410 can comprise a covering/material 21 and the lower, rounded, radially outward extending portion 2000 of the frame 1500, and can form an impermeable or substantially impermeable portion 1404. In one embodiment, this directs blood flow to the valve seat 18 (and a valve once installed or deployed in the valve seat). In one embodiment, blood may be able to flow between the device 10 and the surface 416, i.e., into and out of the areas 2100, until the sealing portion 410 is reached. An optional permeable portion 1400 can allow blood to flow into and out of the area 2130 as indicated by arrows 2132.

Referring to FIGS. 9, 9A, and 9B, the frame 1500 can include one or more of a variety of extensions 5000. As described, the frame 1500 can include one or more extensions 5000 that can be longer than the remainder of the retaining portions 414 and which can be retained by a connector 4914, for example, this can be a lock and release connector 7000 in the outer tube 4910. The extension(s) 5000 are designed such that at least one extension 5000 (e.g., the full extension or a portion of the extension, for example the head 5636) can be retained by the connector 4914. In one embodiment, the extension(s) (e.g., the full extension or a portion thereof) is/are releasably retained between the T-shaped recess 5710 and the door 7020 of the lock and release connector 7000. The extension(s) 5000 allow the position of the frame 1500 to be maintained or otherwise controlled after all or substantially all (e.g., 90% or more) of the frame 1500 has been moved distally past the distal opening 7060 of the outer tube 4910 and/or after the frame 1500 has substantially or completely expanded radially outwardly.

As shown in FIG. 9, the frame 1500 can include two extensions 5000 extending from one end of the frame 1500, such as the proximal end 12. The extensions 5000 can be substantially the same length such that the head 5636 of each extension 5000 are substantially the same distance from the remainder of the frame 1500. In such a configuration, the extensions 5000 can be released from the connector 4914, such as the lock and release connector 7000, at substantially the same time, as described below. The extensions 5000 can be spaced radially around the proximal end 12 of the frame 1500 in any configuration. In the illustrated embodiment, the extensions 5000 are disposed substantially on opposite sides of the frame 1500. However, the extensions 5000 can be disposed in other configurations. For example, there can be any number of equally spaced extensions, any number of unequally spaced extensions, and/or the extensions 5000 can extend from adjacent struts 1502.

As shown in FIG. 9A, the frame 1500 can include one or more first extensions 5000a and one or more second extensions 5000b extending from one end of the frame 1500, such as the proximal end 12. The first and second extensions 5000a, 5000b are longer than the remainder of the optional additional retaining portions 414 and can be retained by the connector 4914, such as the lock and release connector 7000 in the outer tube 4910. The first and second extensions 5000a, 5000b can be substantially similar to the extensions 5000 of FIG. 9; however, the lengths of the first and second extensions 5000a, 5000b can be different from one another. For example, the second extension 5000b can be longer than the first extension 5000a. The first extension 5000a can be the same length as the extensions 5000 of FIG. 9. However, the first extension 5000a can be shorter or longer than the extensions 5000 of FIG. 9. In such a configuration, the first extension 5000a can be released from the connector 4914, such as the lock and release connector 7000, while the second extension 5000b is still retained by the connector 4914, as detailed below. The first and second extensions 5000a, 5000b can be spaced distally around the proximal end 12 of the frame 1500 in any configuration. In the illustrated embodiment, the first and second extensions 5000a, 5000b are disposed substantially on opposite sides of the frame 1500. However, the first and second extensions 5000a, 5000b can be disposed in other configurations. For example, there can be one, two, three, four, five, or any number of first extensions 5000a and one second extension 5000b. For example, there can be any number of equally spaced extensions 5000a, any number of unequally spaced extensions 5000b, and/or the extensions 5000a and/or 5000b can extend from adjacent struts 1502. The various extensions can be spaced radially around the frame in a variety of configurations.

As shown in FIG. 9B, the frame 1500 can include a single extension 5000 extending from one end of the frame 1500, such as the proximal end 12. The extension 5000 can be any size, the extension 5000 can extend proximally beyond the remainder of the frame 1500, and the extension 5000 can be retained by the connector 4914, such as the lock and release connector 7000 in the outer tube 4910. The extension 5000 can be substantially similar to the extensions 5000 of FIG. 9.

While the frame 1500 has been described as having one or two extensions 5000, any number of extensions 5000 can be included. For example, the frame 15000 can include, without limitation, 1, 2, 1 to 2, 2 to 5, 3 to 4, 1 to 6 extensions, or any other number of extensions.

Figure 28A:
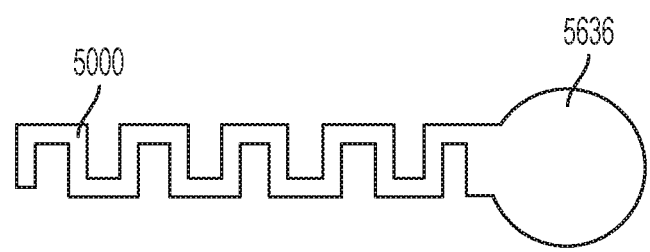
FIG. 28A is a side view of a first exemplary embodiment of an extension, which can be, for example, an extension of the frame of FIG. 9, 9A, or 9B.
Figure 28B:
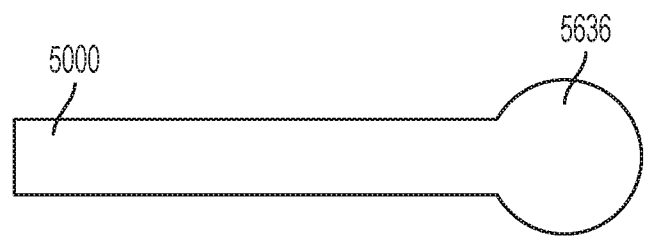
FIG. 28B is a side view of a second exemplary embodiment of an extension, which can be, for example, an extension of the frame of FIG. 9, 9A, or 9B.

FIGS. 28A and 28B show some examples of extensions that can be used. The one or more extensions 5000, or one or more first or second extensions 5000a, 5000b, can take a variety of forms. For example, as shown in FIG. 28A, the extensions 5000 can be spring-like (other spring-like configurations are also possible, e.g., coiled). The inclusion of a spring-like second extension 5000 can permit the frame 1500 to extend smoothly out of the outer tube 4910 as the frame 1500 radially expands as it is distally moved out of the distal opening 7060 of the outer tube 4910. As shown in FIG. 28B, the second extension 5000 can be rod-like and stiffer than the extension of FIG. 28A. The inclusion of a rod-like extension 5000 can permit the frame 1500 to be positioned or otherwise moved as the frame 1500 radially expands as it is distally moved out of the outer tube 4910. However, the one or more second extension 5000 can take other forms as well. For example, the extension 5000 can be curved, twisted, bent, coiled, or otherwise shaped according to the desired deployment and/or control of the frame 1500 out of the outer tube 4910.

Turning now to FIGS. 14A through 16 and FIGS. 29A through 30E, the connector body 4914, such as the connector body of the lock and release connector 7000, can take a variety of forms. Some variety in forms can be based on the proximal end 12 of the frame 1500. For example, the connector body 4914 can have one recess 5710 (e.g., a T-shaped recess) (FIGS. 29A-29C) to hold one extension 5000 or can include multiple recesses to hold multiple extensions (e.g., two T-shaped recesses 5710 to hold two extensions 5000 while the distal end of the frame 1500 expands). Each recess 5710 can include a door 7020 connected (e.g., hingedly connected, flexibly connected, etc.) to the connector body 4914, as described above, to receive the head 5636 of the corresponding extension 5000. The recesses 5710 and doors 7020 can correspond to the number, shape, spacing, and size of the extensions 5000 of the frame 1500. Optionally, one or more fasteners 7040 (See FIG. 16) can be used to connecting the doors 7020 to the connector body 4914. In some embodiments, the fastener 7040 can be a hinge pin. The fastener can be a wire, screw, hinge, suture, tie, pin, etc. The body 7010 and the doors 7020 can be hingedly connected by any fastener known in the art or be flexibly attached.

The connector 4914, such as the lock and release connector 7000, can further comprise a mechanism that can exert a force on the door(s) 7020 to bias the door(s) open (e.g., one or more springs 7050 or similar mechanisms). In some embodiments, the door(s) 7020 can be controlled by one or more control wires to translate the door(s) 7020 from a first position to a second position, including from the closed state to the open state and vice versa. In some embodiments, the door 7020 can be made from shape memory or pseudo-elastic materials, such as shape-memory alloys, including without limitation, a copper-aluminum-nickel alloy, and a nickel-titanium alloy, one example of which includes nitinol. Shape memory materials or superelastic materials can allow the door 7020 to be compressed to a closed state to engage the body 7010, including without limitation a partially closed position, and then when the compression force is released (e.g., when deployed from the catheter), the door 7020 will self-expand back to its pre-compressed open state. In this embodiment, the fastener 7040 can be omitted. For example, the body 7010 and the door(s) 7020 can be integrally formed or fixed together and the door(s) 7020 can flex from a first position to a second position, including from a closed position to an open position.

Turning to FIG. 29A through 29E, the connector 4914 cab include a recess 5710 (e.g., one T-shaped recess or a recess of another type of shape) to receive the head 5636 of an elongated extension 5000, such as the single elongated extension 5000 of FIG. 9B. The length of the recess 5710 can correspond to the length of the elongated extension 5000 and can be longer than the recess 5710 of FIGS. 14A through 16. The cross portion of the recess 5710 can be farther from the distal end of the connector 4914 such that the door 7020 does not move to the open and/or second position until the connector body 4914 is moved further out of the catheter. As the recess 5710 (e.g., a T-shaped recess) is disposed distally farther back on the connector body 4914, the connector assembly 7000 can retain the extension 5000 of the frame 1500 longer as the outer tube/sheath 4910 is moved backward or is retracted relative to the device 10 (or when the stent is moved forward relative to the outer tube 4910) than the connector of FIGS. 14A through 16.

Figure 29C:
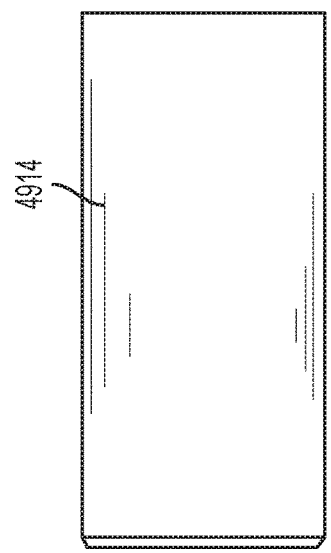
FIG. 29C is a right side view of the connector body of FIG. 29A.
Figure 29B:
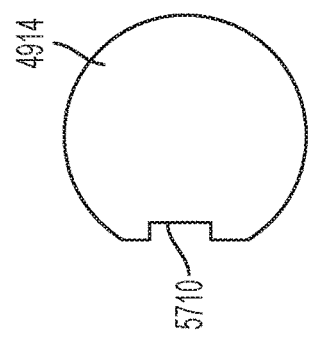
FIG. 29B is a front view of the connector body of FIG. 29A.
Figure 29E:
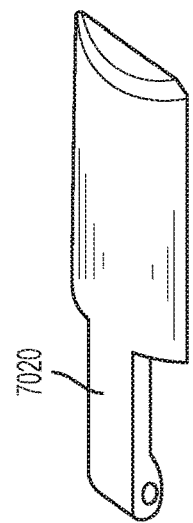
FIG. 29E is a perspective view of an exemplary embodiment of a door of the connector body of FIGS. 29A through 29C.
Figure 29A:
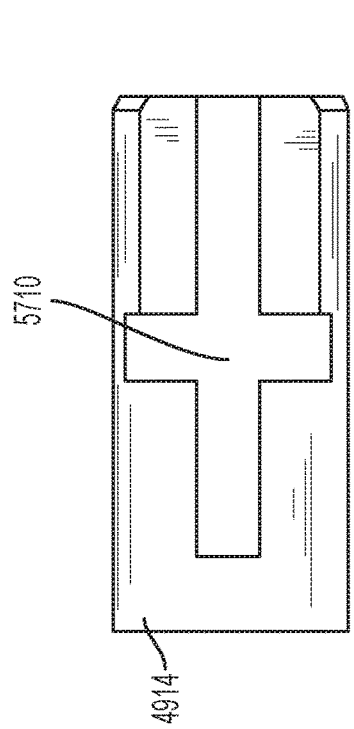
FIG. 29A is a left side view of an exemplary embodiment of a connector body usable with the frame of FIG. 9B.
Figure 29D:
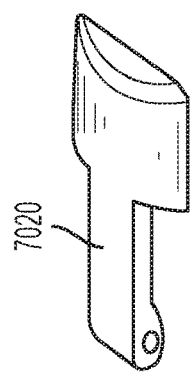
FIG. 29D is a perspective view of an exemplary embodiment of a door for use with the connector body of FIGS. 29A through 29C.

The door 7020 can have a variety of different sizes and shapes. The door 7020 can be shorter, such that the end of the door 7020 does not reach the end of the connector body 4914 (FIG. 29D) or the door 7020 can be longer such that the end of the door 7020 aligns with or extends beyond the end of the connector body 4914 (FIG. 29E). As shown in FIG. 29D, the shorter door 7020 may retain the head 5636 of the elongated extension 5000 while the remainder of the extension 5000 is free. The shorter door 7020 allows the elongated extension 5000 to flex or otherwise adjust more before opening the door 7020 and releasing of the frame 1500. This can permit the frame 1500 to radially expand more smoothly as the frame 1500 is moved distally past the distal opening 7060 of the outer tube 4910. As shown in FIG. 29E, the elongated door 7020 is aligned with the end of the connector body and can retain the head 5636 and a substantial portion of the elongated extension 5000. The elongated door 7020 would allow for more control over the position of the extension 5000 before opening the door 7020 and releasing of the frame 1500. This permits the position of the frame 1500 to more easily be maintained or otherwise controlled as the frame 1500 is moved distally past the distal opening 7060 of the outer tube 4910. In any of these configurations, the elongated extension 5000 of the frame 1500 can be retained by the door 7020 after the frame 1500 has been substantially deployed from the outer tube 4910 and either substantially or completely expanded radially outwardly.

Turning to FIG. 30A through 30E, the connector body 4914 may include a first recess 5710*a* (e.g., a first T-shaped recess or other shape) and a second recess 5710*b* (e.g., a second T-shaped recess or other shape) to receive the heads 5636 of two different length extensions 5000*a*, 5000*b* (e.g. the two heads of FIG. 9B). The first and second recesses 5710*a*, 5710*b* can be disposed on the connector body 4914 in any manner corresponding to the extensions 5000*a*, 500*b* of the frame 1500. In the illustrated embodiment, the first and second recesses 5710*a*, 5710*b* are disposed on substantially opposite sides of the connector body 4914. However, the first and second recesses 5710*a*, 5710*b* can be disposed in other arrangements. For example, the first and second recesses 5710*a*, 5710*b* can be disposed adjacently to correspond to extensions 1500 disposed on adjacent struts 1502 of the frame 1500. The first recess 5710*a* can be covered by a corresponding first door 7020*a* and the second recess 5710*b* can be covered by a corresponding second door 7020*b* hingedly connected to the connector body 4914, such as the lock and release connector 7000, in any manner described above.

The first recess 5710*a* can be elongated to receive the head 5636 of an elongated extension 5000, such as the elongated second extension 5000*b* of FIG. 9A. Similarly to the recess 5710 of FIGS. 29A through 29C, in the T-shaped embodiment shown, the cross portion of the first recess 5710*a* can be disposed proximally farther from the distal end of the connector body 4914 such that the pivot connection of the first door 7020*a* is disposed farther back on the connector body 4914. As the pivot connection of the first door 7020*a* is disposed farther back on the connector body 4914, the first door 7020*a* can retain the extension 5000 of the frame 1500 longer as the outer tube/sheath 4910 is moved backward or is retracted relative to the device 10 (or when the stent is moved forward relative to the outer tube 4910) than the connector of FIGS. 14A through 16. Similar to the doors 7020 of FIGS. 29D and 29E, the first door 7020*a* can be either elongated or shortened.

The second recess 5710*b* can be sized similarly to the recess 5710 of FIGS. 14A through 16 to receive the head 5636 of the shorter extension 5000*a* of FIG. 9A. In the T-shaped embodiment shown, the cross-portion of the second recess 5710*b* and the pivot connection of the door are disposed proximally closer to the distal end of the connector body 4914 than the first recess 5710*a* and the pivot connection of the first door. As the pivot connection of the second door 7020*b* is disposed closer to the distal end of the connector body 4914, the second door 7020*b* can release the extension 5000*a* of the frame 1500 sooner as the outer tube/sheath 4910 is moved backward or is retracted relative to the device 10 (or when the stent is moved forward relative to the outer tube 4910) than the first door 7020*a*.

In use, one elongated extension 5000*b* of the frame 1500 can be retained in the first recess 5710*a* by the first door 7020*a* and one shorter extension 5000*a* of the frame 1500 can be retained in the second recess 5710*b* by the second door 7020*b*. As the outer tube/sheath 4910 is moved backward or is retracted relative to the device 10 (or when the stent is moved forward relative to the outer tube 4910), the second door 7020*b* will move through the distal opening 7060 of the outer tube 4910 and release the retained extension 5000a, while the elongated extension 5000b is retained in the first recess 5710a by the first door 7020a. While the elongated extension 5000b is maintained in the first recess 5710a, the position of the frame 1500 can be maintained or otherwise controlled. Once the frame 1500 is radially expanded in the desired position, the outer tube/sheath 4910 can then be moved backward or retracted relative to the device 10 (or the stent can be moved forward relative to the outer tube 4910) such that the first door 7020a is moved distally past the distal opening 7060 of the outer tube 4910 and thereby release the elongated extension 5000b. The sequential release of the extensions 5000a, 5000b can permit the frame 1500 to radially expand more smoothly as the frame 1500 is moved distally past the distal opening 7060 of the outer tube 4910 and may permit the position of the frame 1500 to more easily be maintained or otherwise controlled as the frame 1500 is moved distally past the distal opening 7060 of the outer tube 4910.

Having only one extension or only one elongated extension on a self-expandable frame acts to help prevent the frame from jumping out of the distal end of the catheter and throwing off the placement. As the proximal end of the frame approaches the distal opening of the delivery catheter, forces can build between the proximal end of the frame and distal opening of the catheter that can cause the frame to jump forward out of the catheter. Having multiple extensions at the proximal-most end of the frame can make jumping more likely, as the extensions can act against each other and create opposing forces against the distal end of the catheter. When the frame has only one elongated extension (e.g., with or without additional shorter extensions) or only one extension at all, the frame is allowed to fully expand while retained by only one extension, then this one remaining extension can release the frame without causing jumping.

In view of the many possible embodiments to which the principles of the disclosed invention can be applied, it should be recognized that the illustrated embodiments are only preferred examples of the invention and should not be taken as limiting the scope of the invention. All combinations and subcombinations of features of the foregoing exemplary embodiments are contemplated by this application. Similarly, all combinations and subcombinations of steps/methods of the foregoing examples are contemplated as well and the steps described can be combined in various ways and orders. The scope of the invention is defined by the following claims. We therefore claim as our invention all that comes within the scope and spirit of these claims.

The invention claimed is:

1. A system comprising:
a lock and release connector comprising a body, at least one door engaged with the body, and at least one fastener connecting at least one end of the door to the body, wherein the door is moveable from a first position to a second position;
an outer tube having a distal opening;
an implantable medical device disposed in the outer tube wherein the medical device has an extension; and
wherein the extension is interposed between the body and the door.

2. A system comprising:
a lock and release connector comprising a body, at least one door engaged with the body, and at least one spring exerting force on the door, wherein the door is moveable from a first position to a second position;
an outer tube having a distal opening;
an implantable medical device disposed in the outer tube wherein the medical device has an extension; and
wherein the extension is interposed between the body and the door.

3. The system of claim 2, wherein the door is integral with the body.

4. The system of claim 2, wherein the door is connected to the body.

5. The system of claim 1, wherein the door is hingedly connected to the body.

6. The system of claim 2, wherein the door comprises a shape memory material.

7. The system of claim 2, further comprising at least one fastener connecting at least one end of the door to the body.

8. The system connector of claim 1, wherein the door is actively controlled to move from the first position to the second position.

9. A system comprising:
a lock and release connector comprising a body, at least one door engaged with the body, and a wire, a screw, a separate hinge, or a pin connecting the body and the door, wherein the door is moveable from a first position to a second position;
an outer tube having a distal opening;
an implantable medical device disposed in the outer tube wherein the medical device has an extension; and
wherein the extension is interposed between the body and the door.

10. The system of claim 1, further comprising a second door moveable from a first position to a second position;
wherein the first and second doors are sequentially moveable from the respective first position to the respective second position.

11. A lock and release connector for a trans-catheter implantable device comprising:
a body;
at least one door engaged with the body, wherein the door is moveable from a first position to a second position; and
at least one fastener connecting at least one end of the door to the body.

12. A lock and release connector for a trans-catheter implantable device comprising:
a body;
at least one door engaged with the body, wherein the door is moveable from a first position to a second position; and
at least one spring exerting force on the door.

13. The lock and release connector of claim 12, wherein the door is integral with the body.

14. The lock and release connector of claim 12, wherein the door is connected to the body.

15. The lock and release connector of claim 11, wherein the door is hingedly connected to the body.

16. The lock and release connector of claim 12, wherein the door comprises a shape memory material.

17. The lock and release connector of claim 12, wherein the door comprises a nickel titanium alloy.

18. The lock and release connector of claim 12, further comprising at least one fastener connecting at least one end of the door to the body.

19. The lock and release connector of claim 11, wherein the door is actively controlled to move from the first position to the second position.

20. A lock and release connector for a trans-catheter implantable device comprising:
a body;

at least one door engaged with the body, wherein the door is moveable from a first position to a second position; and a wire, a screw, a separate hinge, or a pin connecting the body and the door.

21. The lock and release connector of claim 11, further comprising a second door moveable from a first position to a second position;

wherein the first door and the second door are sequentially moveable from the respective first position to the respective second position.

22. The lock and release connector of claim 21, further configured to move the first door to the second position such that a first extension of an implantable medical device can be released therefrom while a second extension continues to be held under the second door.

23. The system of claim 9, wherein the door is hingedly connected to the body.

24. The system connector of claim 9, wherein the door is actively controlled to move from the first position to the second position.

25. The system of claim 9, further comprising a second door moveable from a first position to a second position;

wherein the first and second doors are sequentially moveable from the respective first position to the respective second position.

26. The system of claim 2, wherein the door is hingedly connected to the body.

27. The system connector of claim 2, wherein the door is actively controlled to move from the first position to the second position.

28. The system of claim 2, further comprising a second door moveable from a first position to a second position;

wherein the first and second doors are sequentially moveable from the respective first position to the respective second position.

29. The lock and release connector of claim 20, wherein the door is hingedly connected to the body.

30. The lock and release connector of claim 20, wherein the door is actively controlled to move from the first position to the second position.

31. The lock and release connector of claim 20, further comprising a second door moveable from a first position to a second position;

wherein the first door and the second door are sequentially moveable from the respective first position to the respective second position.

32. The lock and release connector of claim 31, further configured to move the first door to the second position such that a first extension of an implantable medical device can be released therefrom while a second extension continues to be held under the second door.

33. The lock and release connector of claim 12, wherein the door is hingedly connected to the body.

34. The lock and release connector of claim 12, wherein the door is actively controlled to move from the first position to the second position.

35. The lock and release connector of claim 12, further comprising a second door moveable from a first position to a second position;

wherein the first door and the second door are sequentially moveable from the respective first position to the respective second position.

36. The lock and release connector of claim 35, further configured to move the first door to the second position such that a first extension of an implantable medical device can be released therefrom while a second extension continues to be held under the second door.

\* \* \* \* \*